US006805861B2

(12) United States Patent \
Stauss

(10) Patent No.: US 6,805,861 B2 \
(45) Date of Patent: Oct. 19, 2004

(54) IMMUNOTHERAPY USING CYTOTOXIC T LYMPHOCYTES (CTL)

(75) Inventor: Hans Josef Stauss, London (GB)

(73) Assignee: Imperial College Innovations Limited, London (GB)

( * ) Notice: Subject to any disclaimer, the term of this patent is extended or adjusted under 35 U.S.C. 154(b) by 0 days.

(21) Appl. No.: 09/101,413

(22) PCT Filed: Jan. 17, 1997

(86) PCT No.: PCT/GB97/00118

§ 371 (c)(1),
(2), (4) Date: Aug. 7, 1998

(87) PCT Pub. No.: WO97/26328

PCT Pub. Date: Jul. 24, 1997

(65) Prior Publication Data

US 2002/0090362 A1 Jul. 11, 2002

(30) Foreign Application Priority Data

Jan. 17, 1996 (GB) ................................. 9600878 \
Nov. 12, 1996 (GB) ................................. 9623471

(51) Int. Cl.$^7$ ............................................. A01N 63/00
(52) U.S. Cl. ................................ 424/93.71; 424/93.21; 435/372.3
(58) Field of Search .................... 435/372.3; 424/93.21, 424/93.71

(56) References Cited

U.S. PATENT DOCUMENTS

| | | | |
|---|---|---|---|
| 4,690,915 A | | 9/1987 | Rosenberg |
| 4,844,893 A | | 7/1989 | Honsik et al. |
| 5,081,029 A | | 1/1992 | Zarling et al. |
| 5,359,046 A | | 10/1994 | Capon et al. |
| 5,731,160 A | * | 3/1998 | Melief et al. |
| 5,928,639 A | * | 7/1999 | Slavin et al. |
| 5,994,523 A | * | 11/1999 | Kawakami et al. |

FOREIGN PATENT DOCUMENTS

| | | |
|---|---|---|
| EP | 257962 | 2/1988 |
| EP | 360205 | 3/1990 |
| EP | 415666 | 6/1991 |
| EP | 523948 | 1/1993 |
| JP | 61176529 | 8/1986 |
| JP | 10 218093 | 7/1999 |
| WO | WO 91/04317 | 4/1991 |
| WO | WO 91/07509 A1 | 5/1991 |
| WO | WO 9201459 | 2/1992 |
| WO | WO 92/05794 | 4/1992 |
| WO | WO 93/17095 | 9/1993 |
| WO | WO 94/21287 | 9/1994 |
| WO | WO 95/04817 | 2/1995 |
| WO | WO 95/22561 | 8/1995 |
| WO | WO 95/29995 A1 | 11/1995 |
| WO | WO 95/18969 | 7/1996 |
| WO | WO 97/26328 A1 | 7/1997 |
| WO | WO 00/06602 A1 | 2/2000 |
| WO | WO 00/18795 A2 | 4/2000 |

OTHER PUBLICATIONS

Kohlen et al. Cancer Immunol Immunother. 26: 74–82, 1988.* \
Wu et al. J. Biol. Chem. 220: 5944, 1995.* \
Huans et al. Cancer Immunol. Immunother. 36: 399, 1994.* \
Yin et al. Eur. J. Immunol. 24: 1988, 1994.* \
Falkenburg J Immunotherapy 14:305–309, 1993.* \
Dahl, et al., "Normal Self Proteins as Targets for Tumour Specific Cytotoxic Lymphocytes (CTL)," $9^{th}$ International Congress of Immunology, San Francisco, CA, USA 607 (1995). \
Dahl, et al., "A synthetic peptide derived from the tumor–associated protein mdm2 can stimulate autoreactive, high avidity cytotoxic T lymphocytes that recognize naturally processed protein," *J Immunol* 157(1):239–46 (1996). \
Hill, et al., "Class I major histocompatibility complex–restricted cytotoxic T lymphocytes specific for Epstein–Barr virus (EBV)–transformed B lymphoblastoid cell lines against which they were raised," *J Exp Med* 181(6):2221–8 (1995). \
Hsu, et al., "Vaccination of patients with B–cell lymphoma using autologous antigen–pulsed dendritic cells," *Nat Med* 2(1):52–8 (1996). \
Inoue, et al., "Long–term follow–up of minimal residual disease in leukemia patients by monitoring WT 1 (Wilms tumor gene) expression levels," *Blood* 88(6):2267–78 (1996). \
Jerome, et al., "Tumor–specific cytotoxic T cell clones from patients with breast and pancreatic adenocarcinoma recognize EBV–immortalized B cells transfected with polymorphic epithelial mucin complementary DNA," *J Immunol* 151(3): 1654–62 (1993). \
Kawakami, et al., "Shared human melanoma antigens. Recognition by tumor–infiltrating lymphocytes in HLA–A2.1–transfected melanomas," *J Immunol* 148(2):638–43 (1992).

(List continued on next page.)

*Primary Examiner*—G. R. Ewoldt \
(74) *Attorney, Agent, or Firm*—Pabst Patent Group LLP

(57) ABSTRACT

A method of treating a patient with a disease wherein the patient contains diseased cells which cells contain, or are associated with, an abnormal molecule or an abnormally elevated amount of a molecule and which cells are capable of presenting at least part of said molecule on their surface by an HLA class I (or equivalent) molecule, the method comprising administering to the patient a therapeutically effective amount of cytotoxic T lymphocytes (CTL) which recognize at least part of said molecule when presented by an HLA class I (or equivalent) molecule on the surface of a cell characterized in that the cytotoxic T lymphocytes are not derived from the patient with a disease. Preferably, the CTL are derived from an individual which individual does not carry the HLA class I (or equivalent) molecule type which, in the patient, presents at least part of said abnormal molecule, or molecule abnormally elevated, contained in or associated with the disease cells of said patient.

12 Claims, 7 Drawing Sheets

OTHER PUBLICATIONS

Kwak, et al., "Transfer of myeloma idiotype–specific immunity from an actively immunised marrow donor," *Lancet* 345(8956):1016–20 (1995).

Lu, et al., "Improved Synthesis of 4–Alkoxybenzyl Alcohol Resin," *J. Org. Chem.* 46: 3433–3436 (1981).

Melief, Prospects of T–cell immunotherapy for cancer by peptide vaccination, *Semin Hematol* 30(3 Suppl 3):32–3 (1993).

Mennsen, et al., "Presence of Wilms' tumor gene (wt1) transcripts and the WT1 nuclear protein in the majority of human acute leukemias," *Leukemia* 9(6):1060–7 (1995).

Murphy, et al., "Phase I clinical trial: T–cell therapy for prostate cancer using autologous dendritic cells pulsed with HLA–A0201–specific peptides from prostate–specific membrane antigen," *Prostate* 29(6):371–80 (1996).

Peoples, et al., "Breast and ovarian cancer–specific cytotoxic T lymphocytes recognize the same HER2/neu–derived peptide," *Proc Natl Acad Sci U S A* 92(2):432–6 (1995).

Plebanski, et al., "Induction of peptide–specific primary cytotoxic T lymphocyte responses from human peripheral blood," *Eur J Immunol* 25(6):1783–7 (1995).

Rodeck, et al., "Expression of the wt1 Wilms' tumor gene by normal and malignant human melanocytes," *Int J Cancer* 59(1):78–82 (1994).

Shimamoto, et al., "The expression pattern of erythrocyte/megakaryocyte–related transcription factors GATA–1 and the stem cell leukemia gene correlates with hematopoietic differentiation and is associated with outcome of acute myeloid leukemia," *Blood* 86(8):3173–80 (1995).

Tamaki, et al., "Increased expression of the Wilms tumor gene (WT1) at relapse in acute leukemia," *Blood* 88(11):4396–8 (1996).

Viel, et al., "Molecular mechanisms possibly affecting WT1 function in human ovarian tumors," *Int J Cancer* 57(4):515–21 (1994).

Yang, et al. "Major Histocompatability Complex (MHC)–encoded HAM2 Is Necessary for Antigenic Peptide Loading onto Class 1 MHC Molecules" *J. Biol. Chem.* 267: 11669–11672 (1992).

Alexander, et al., "Differential Transport Requirements of HLA and H–2 Class I Glycoproteins," *Immunogenetics* 29:380–388 (1989).

Bakker, et al., "Melanocyte Lineage–Specific Antigen gp100 is Recognized by Melanoma–Derived Tumor–Infiltrating Lymphocytes," *J. Exp. Med.* 179:1005–1009 (1994).

Boël, et al., "BAGE: a New Code Encoding an Antigen Recognized on Human Melanomas by Cytolytic T Lymphocytes," *Immunity* 2(2):167–175 issn. 1074–7613 (1995).

Chung, et al., "Functional Three–Domain Single–Chain T–Cell Receptors," *Proc. Natl. Acad. Sci. USA* 91:12654–12658 (1994).

Cox, et al., "Identification of a Peptide Recognized by Five Melanoma–Specific Human Cytotoxic T Cell Lines," *Science* 264:716–719 (1994).

Eshhar, et al., "Specific Activation and Targeting of Cytotoxic Lymphocytes Through Chimeric Single Chains Consisting of Antibody–Binding Domains and the ( or . Subunits of the Immunoglobulin and T–Cell Receptors," *Proc. Natl. Acad. Sci. USA* 90(N2): 720–724 (1993).

Faber, et al., "Generation of Leukemia–reactive Cytotoxic T Lymphocyte Clones from the HLA–identical Bone Marrow Donor of a Patient with Leukemia," *J. Exp. Med.* 176(5):1283–1289 (1992).

Falkenburg, et al., "Generation of Donor–Derived Antileukemic Cytotoxic T–Lymphocyte Responses for Treatment of Relapsed Leukemia After Allogeneic HLA–Identical Bone Marrow Transplantation," *J. Immunotherapy* 14(4):305–309 issn. 1053–8550 (1993).

Fidler & Nicholson, "*Brief Communication*: Organ Selectivity for Implantation Survival and Growth of B16 Melanoma Variant Tumor Lines," *J. Natl. Cancer Inst.* 57:1199–1202 (1976).

Finer, et al., "kat: A High–Efficiency Retroviral Transduction System for Primary Human T Lymphocytes," *Blood* 83:43–50 (1994).

Gagliardi, et al., "Presentation of peptides by cultured monocytes or activated T cells allows specific priming of human cytotoxic T lymphocytes in vitro," *Intl. Immunol.*, 7(11):1741–1752 (1995).

Goldman, "Allogenic Bone Marrow Transplantation: State of the Art and Future Directions," *Bone Marrow Transplant* 1:133–134 (1989).

Heath, et al., "Peptide–dependent recognition of $H–2K^b$ by alloreactive cytotoxic T lymphocytes," *Nature*, 341(6244):749–752 (1989).

Hwu, et al., "Lysis of Ovarian Cancer Cells by Human Lymphocytes Redirected with a Chimeric Gene Composed of an Antidody Variable Region and the Fc Receptor Chain," *J. Exp. Med.* 178:361–366 (1993).

Kast, et al., "Eradication of Adenovirus E1–Induced Tumors by E1A–Specific Cytotoxic T Lymphocytes," *Cell* 59(4):603–614 (1989).

Kawakami, et al., "Identification of a human melanoma antigen recognized by tumor–infiltrating lymphocytes associated with in vivo tumor rejection," *Proc. Natl. Acad. Sci. USA* 91(14):6458–6462 (1994).

Kawakami, et al., "Cloning of the Gene Coding for a Shared Human Melanoma Antigen Recognized by Autologous T Cells Infiltrating into Tumor," *Proc. Natl. Acad. Sci. USA* 91(9):3515–3519 (1984).

Kawakami, et al., "Indentification of the Immunodominant Peptides of the MART–1 Human Melanoma Antigen Recognized by the Majority of HLA–A2–Restricted Tumor Infiltrating Lymphocytes," *J. Exp. Med.* 180:347–352 (1994).

Ljunggren & Kärre, "Host Resistance Directed Selectively Against H–2–Deficient Lymphoma Variants," *J. Exp. Med.* 162:1745–1759 (1985).

Moritz, et al., "Cytotoxic T Lymphocytes with a Grafted Recognition Specificity for ERBB2–Expressing Tumor Cells," *Proc. Natl. Acad. Sci. USA* 91:4318–4322 (1994).

Nixon & McMichael, "Cytotoxic T–Cell Recognition of HIV Proteins and Peptides," *AIDS* 5(9):1049–1059 (1991).

Nowak, et al., "Antigenic Oscillations and Shifting Immunodominance in HIV–1 Infections," *Nature* 375(6532):606–611 (1995).

Riddell, et al., "Restoration of Viral Immunity in Immunodeficient Humans by the Adoptive Transfer of T Cell Clones," *Science* 257(5067):238–241 (1992).

Roberts, et al., "Targeting of Human Immunodeficiency Virus–Infected Cells by CD8+ T Lymphocytes Armed with Universal T–Cell Receptors," *Blood* 84:2878–2889 (1994).

Rojo, et al., "Peptide–Mediated Allo–Recognition of HLA–B27 by Cytotoxic T Lymphocytes," *Int. J. Cancer: Suppl.* 6:10–13 (1991).-

Stauss and Dahl, "Cellular Oncogenes for Tumour Immunity: Immunotherapy," *Tumour Immunology*, Dalgleish/Browning, Chapter 7 (1995).

Theobald, et al., "Targeting p53 as a General Tumor Antigen," *Proc. Natl. Acad. Sci. USA* 92:11993–11997 (1995).

Torpey, et al., "Effects of Adoptive Immunotherapy with Autologous CD8+ T Lymphocytes on Immunologic Parameters: Lymphocyte Subsets and Cytotoxic Activity," *Clin. Immunol. Immunopathol.* 68(3):263–272 (1993).

Traversari, et al., "A Nonapeptide Encoded by Human Gene MAGE–1 Is Recognized on HLA–A1 by Cytolytic T Lymphocytes Directed Against Tumor Antigen M22–E," *J. Exp. Med.* 176:1453–1457 (1992).

van der Bruggen, et al., "A Gene Encoding an Antigen Recognized by Cytolytic T Lymphocytes on a Human Melanoma," *Science* 254:1643–1647 (1991).

van Lochem, et al., "In vitro separation of host specific graft–versus–host and graft–versus–leukemia cytotoxic T cell activities," *Bone–Marrow–Transplantation* 10(2):181–183 (1992).

Walker & Plata, "Editorial Review: Cytotoxic T Lymphocytes Against HIV," *AIDS* 4(3):177–184 (1990).

Wölfel, et al., "Two Tyrosinase Nonapeptides Recognized on HLA–A2 Melanomas by Autologous Cytolytic T Lymphocytes," *Eur. J. Immunol.* 24:759–764 (1994).

Al–Obeidi, et al., "Peptide and peptidomimetic libraries," *Molecular Biotechnology* 9:205–223 (1998).

Beeley, "Peptidomimetics and small–molecule drug design: towards improved bioavailabilty and in vivo stability," *TIBTECH* 12:213–216 (1994).

Bluyssen, et al., "The interferon–stimulated gene 54 K promoter contains two adjacent functional interferon–stimulated response elements of different strength, which act synergistically for maximal interferon–alpha inducibility," *Eur. J. Biochem* 220: 395–402 (1994).

Bottger, et al., "Molecular characterization of the hdm2–p53 interaction," *J Mol Biol* 269:744–756 (1997).

Buckler, et al., "Isolation, Characterization, and Expression of the Murine Wilms' Tumor Gene (WT1) During Kidney Development," *Molecular and Cellular Biology* 11(3): 1707–1712 (1991).

Crossley & Orkin, "Phosphorylation of the Erythroid Transcription Factor GATA–1," *J Bio Chem* 269:16589–96 (1994).

Gaiger, et al., "Immunity to WT1 in the animal model and in patients with acute myeloid leukemia," *Blood* 96(4):1480–89 (2000).

Gao, et al., "Selective elimination of leukemic CD34+ progenitor cells by cytotoxic T lymphocytes specif for WT1," *Blood* 95:2198–2203 (2000).

Janeway, et al., *Immunobiology* $4^{th}$ Edition (Austin et al., eds.), pp. 121, 551, 569, Figures 4.3, 4.5 and 4.7, Garland Press 1999.

Kieber–Emmons, et al., "Therapeutic peptides and peptidomimetics," *Curr Opinion Biotechnol* 8:436–441 (1997).

Meziere, et al., "In vivo helper cell response to retro–inverso peptidomimetics," *Journal of Immunology* 159:3230–37 (1997).

Murali & Greene, "Structure–based design of immunologically active therapeutic peptides," Immunolgic Research 17(1&2):163–169 (1998).

Nakanishi, et al., "Peptidomimetics of the immunolglobin supergene family—a review," *Gene* 137:51–56 (1993).

Ohminami, et al., "HLA class I–restricted lysis of leukemia cells by a CD8+ cytotoxic T–lymphocyte clone specific for WT1 peptide," *Blood* 95:286–93 (2000).

Oka, et al., "Cancer Immunotherapy targeting Wilms' Tumor Gene WT1 product," *J Immunol* 164:1873–80 (2000).

Oka, et al., "Human cytotoxic T–lymphocyte responses specific for peptides of the wild–type Wilms tumor (WT1) product," *Immunogenetics* 51:99–107 (2000).

Sadovnikova & Stauss, "Peptide–specific cytotoxic T lymphocytes restricted by nonself major histocompatibilty complex class I molecules: reagents for tumor immunotherapy," *Proc Natl Acad Sci USA* 93:13114–13118 (1996).

Semba, et al., "cDNA cloning and its pronephros–specific expression of the Wilms' tumor suppressor gene, WT1, from *Xenopus laevis,*" *Gene* 175: 167–172 (1996).

Sharma, et al., "Molecular Cloning of Rat Wilms' Tumor Complementary DNA and a Study of Messenger RNA Expression in the Urogenital System and the Brain," *Cancer Research* 52: 6407–6412 (1992).

* cited by examiner

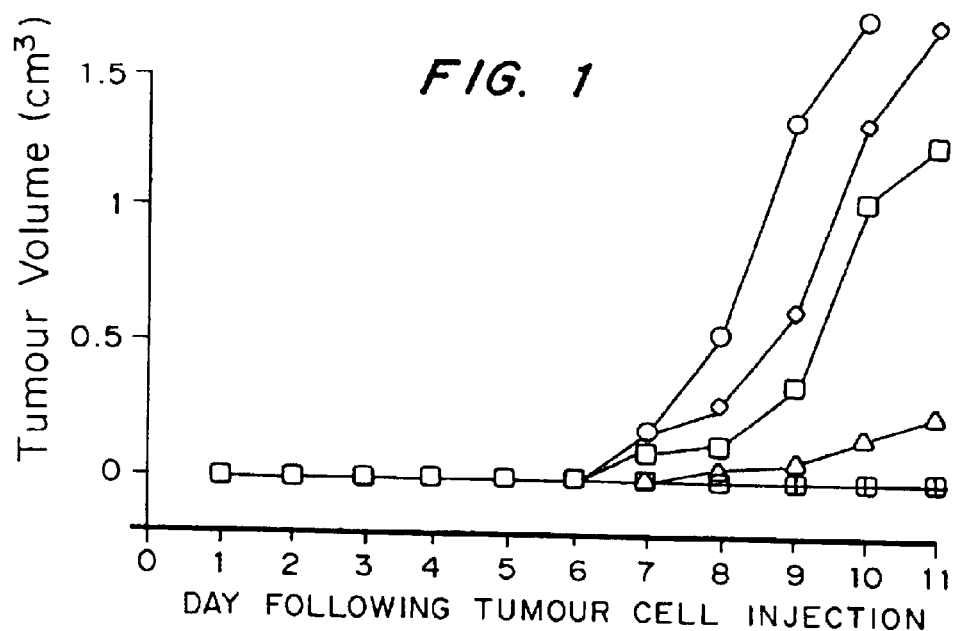
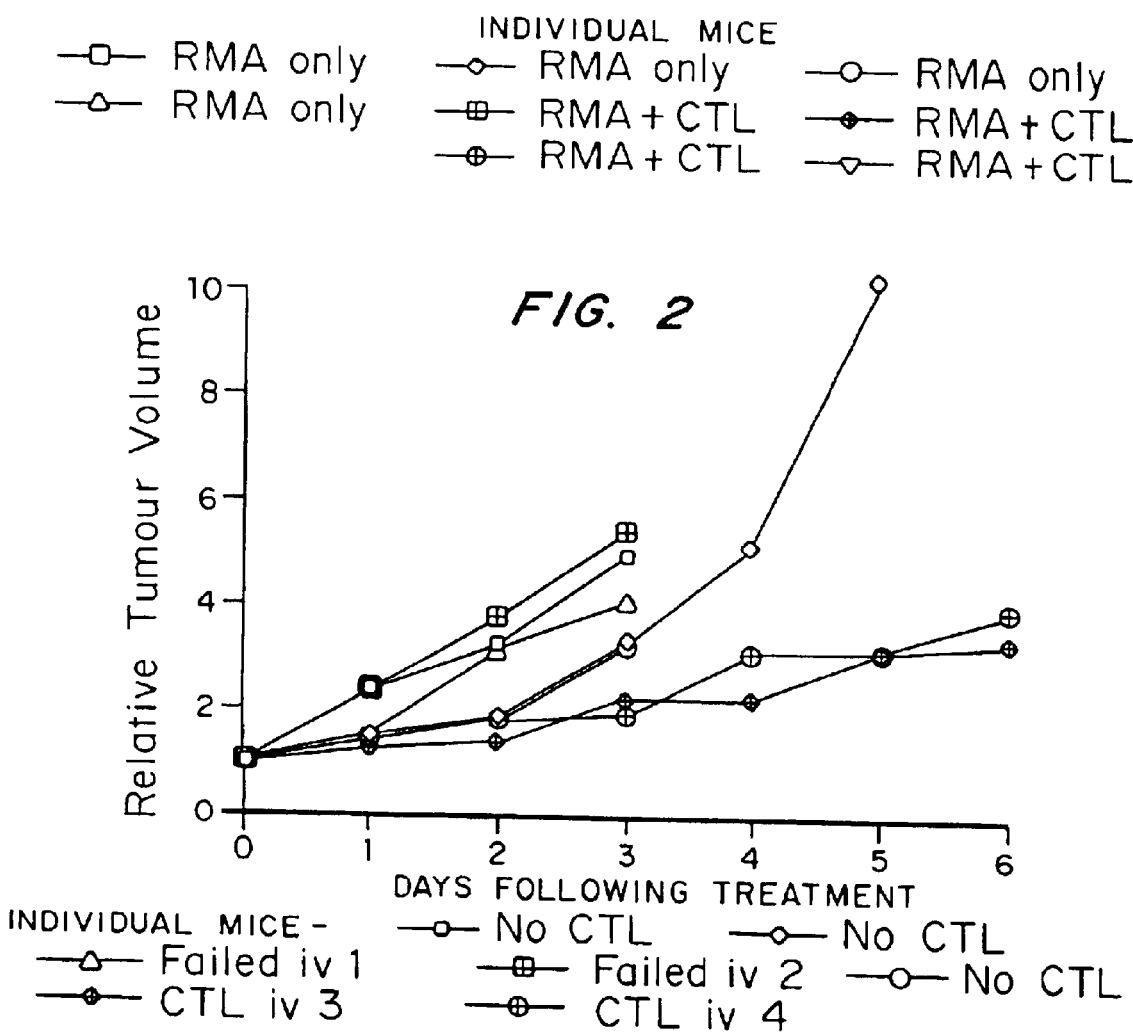

IMMUNOTHERAPY USING CYTOTOXIC T LYMPHOCYTES (CTL)

The present invention relates to immunotherapy, particularly to immunotherapy using cytotoxic T lymphocytes (CTL), and more particularly to adoptive immunotherapy.

There is evidence that anti-tumour CTL and anti-virus CTL play an important role in vivo. Tumour-reactive CTL have been shown to mediate tumour regression in animal models (1) and in man (2). Similarly, recent studies suggest that HIV-specific CTL may limit HIV virus load in vivo (3).

There is much interest in using in vitro generated CTL for adoptive immunotherapy of cancer. The potential importance of in vitro generated CTL is suggested in experiments with adenovirus transformed murine tumour cells (1). Nude mice were injected with tumour cells and large tumours were allowed to form. Tumour regression was observed when these mice were treated with CTL specific for the transforming E1A protein expressed in the tumour cells. Similarly, when in vitro generated CTL specific for gp100 were given to a melanoma patient tumour regression was observed (2). Thus, it is believed that adoptive transfer of T lymphocytes with defined specificity represents a promising therapy for cancer patients. Similarly, adoptively transferred CTL specific for cytomegalovirus seem to suppress CMV infection in patients who underwent bone marrow transplantation (4).

WO 93/17095 describes a method of producing, loading and using MHC class I molecules to specifically activate CTL derived from a patient in vitro and then returning the patient's activated CTL in a form of treatment. WO 93/17095 specifically teaches that it is the patients own CTL that should be used to treat the patient.

Chung et al (1994) *Proc. Natl. Acad. Sci. USA* 91, 12654–12658 describes the production of functional three-domain single-chain T-cell receptors.

Moritz et al (1994) *Proc. Natl. Acad. Sci. USA* 91, 4318–4322 describes CTL with a grafted recognition specificity for ERBB2-expressing tumour cells.

Roberts et al (1994) *Blood* 84, 2878–2889 describes the targeting of HIV-infected cells by $CD8^+$ T lymphocytes armed with "universal" (chimaeric) T-cell receptors.

U.S. Pat. No. 5,359,046 describes "universal" (chimaeric) T-cell receptors.

Faber et al (1992) *J. Exp. Med.* 176, 1283–1289 describes the generation of leukaemia-reactive CTL clones from genotypically HLA-identical bone marrow donor of a patient with leukaemia. In prior art allogeneic bone marrow transplantations the material comes directly from a healthy donor, and so is a mixed population and is not cloned.

A major rate limiting step of current adoptive immunotherapy is that it is patient-specific and dependent upon the isolation and in vitro expansion of specific CTL from the patient's own T lymphocyte pool. Thus, for each patient elaborate time-consuming and expensive in vitro work is required to generate sufficient numbers of specific CTL. Furthermore, in some patients the immune system may be severely suppressed, and it may be impossible to isolate specific CTL.

The present invention is aimed at overcoming these limitations and providing more efficient and potentially more effective adoptive immunotherapy with cytotoxic T lymphocytes (CTL) of patients, particularly cancer patients.

A first aspect of the invention provides a method of treating a patient with a disease wherein the patient contains diseased cells which cells contain, or are associated with, an abnormal molecule or an abnormally elevated amount of a molecule and which cells are capable of presenting at least part of said molecule on their surface by an HLA class I (or equivalent) molecule, the method comprising administering to the patient a therapeutically effective amount of cytotoxic T lymphocytes (CTL) which recognise at least part of said molecule when presented by an HLA class I (or equivalent) molecule on the surface of a cell characterised in that the cytotoxic T lymphocytes are not derived from the patient with a disease.

Thus the present invention overcomes the previous problems by, for example, generating CTL from, preferably, healthy individuals against selected peptides presented by the patient's HLA class I molecules. These CTL may be allo-restricted if the CTL donor does not express the class I molecule that presents the CTL recognised peptides, or they may be self MHC(HLA)-restricted if the CTL donor expresses the class I molecule that presents the CTL recognised peptides.

The CTL for administering to the patient are conveniently made using the method of the third aspect of the invention as described below.

By "HLA class I (or equivalent molecule)" we mean a HLA class I protein or any protein which is equivalent to a human HLA class I molecule from any other animal, particularly a vertebrate and especially a mammal. For example it is well known that in the mouse the MHC class I proteins are similar in structure to, and fulfill a similar role to, the human HLA class I proteins. Equivalent proteins to human HLA class I molecules can be readily identified in other mammalian species by a person skilled in the art, particularly using molecular biological methods.

By "at least part of said molecule" we include any fragment of said molecule that can be presented on the surface of a cell by an HLA class I (or equivalent) molecule.

By "an abnormally elevated amount of a molecule" we mean that in a diseased cell, compared to a normal cell, the molecule is present at >1.2 times the concentration; more preferably >2 times; still more preferably >5 times and most preferably >10 times the concentration. It will be clear that an abnormally elevated amount of a molecule includes the situation where normal (ie wild type) molecules are expressed in cell types where that molecule is not usually expressed (ie presence vs absence). Also, it will be clear that the abnormally elevated amount of a molecule may be due to abnormal activation of expression of a polypeptide which is not normally expressed in a cell or it may be due to an abnormal level of expression.

It is particularly preferred if the CTL administered to the patient is a clonal population of CTL.

It is also particularly preferred if the CTL (preferably a clonal population of CTL) administered to the patient are substantially free of other cell types.

The molecule may be any molecule at least part of which can be presented on the surface of a cell by an HLA class I (or equivalent) molecule.

Preferably, the molecule is a polypeptide including a carbohydrate-containing polypeptide such as a glycoprotein or is a carbohydrate including a peptide-containing carbohydrate, or is a lipid or glycolipid including a peptide-containing lipid or glycolipid.

As discussed in more detail below, abnormal molecules or an abnormally elevated amount of a molecule are associated with many diseases and diseased cells.

The method is particularly advantageous as it is effective in targeting self proteins (for example, those which are overexpressed in the diseased cell or are expressed in a disease cell whereas in a normal cell of the same type they are not expressed).

The patient may or may not be immuno-suppressed when receiving the CTL. It is preferred if the patient is immuno-suppressed.

It is more preferred if the said molecule is a polypeptide. It is well known in the art of immunology that peptide fragments derived from larger peptides or polypeptides are presented by HLA class I (or equivalent) molecules on the surface of a cell, especially diseased cells.

Although the CTL may be derived from the individual who is the patient from a sample taken before the patient acquired the disease, it is most preferred if the CTL are derived from an individual other than the patient.

Of course, it is preferred that the individual is a healthy individual. By "healthy individual" we mean that the individual is generally in good health, preferably has a competent immune system and, more preferably, is not suffering from any disease which can be readily tested for, and detected.

In a particularly preferred embodiment the CTL are derived from an individual which individual does not carry the HLA class I (or equivalent) molecule type which, in the patient, presents at least part of said abnormal molecule, or molecule abnormally elevated, contained in or associated with the diseased cells of said patient.

The word "type" is used in the conventional immunological sense.

Thus, the CTL are derived from an individual whose HLA class I (or equivalent) molecules are mismatched with those of the patient. Thus, it is preferred if the CTL are allo-restricted.

In this preferred embodiment the HLA class I (or equivalent) molecule types, other than the type that presents at least part of said abnormal molecule or said molecule abnormally elevated, may be the same or different as between the patient and the individual. In certain circumstances it is preferred if they are the same.

Mutant polypeptides, as are described in more detail below, are often associated with diseased cells and often serve as a molecular marker for the diseased cell. Thus, it is preferred if the polypeptide is a mutant polypeptide associated with said diseased cells.

Diseased cells, as described in more detail below, are often associated with the presence of a polypeptide at a higher level in said diseased cells compared to non-diseased cells. For example, certain polypeptides are known to be overexpressed in some tumour cells. Thus, it is also preferred to target non-mutant self proteins.

It is preferred if the polypeptides are any of the following:

i) normal cellular proteins that are expressed at abnormally high levels in tumours; eg cyclin D1 in a variety of tumours; cyclin E in breast cancer; mdm 2 in a variety of tumours; EGF-R, erb-B2, erb-B3, FGF-R, insulin-like growth factor receptor, Met, myc, p53 and BCL-2 are all expressed in various tumours.

ii) normal cellular proteins that are mutated in tumours; eg Ras mutations in a variety of tumours; p53 mutations in a variety of tumours; BCR/ABL translocation in CML and ALL; CSF-1 receptor mutations in AML and MDS; APC mutations in colon cancer; RET mutations in MEN2A, 2B and FMTC; EGFR mutations in gliomas; PML/RARA translocation in PML; E2APBX1 translocation in pre B leukaemias and in childhood acute leukaemias.

iii) virally encoded proteins in tumours associated with viral infection; eg human papilloma virus proteins in cervical cancer; Epstein-Barr virus proteins in B cell lymphomas and Hodgkin's lymphoma; HTLV-1 proteins in adult T cell leukaemia; hepatitis B and C virus proteins in hepatocellular carcinoma; herpes-like virus proteins in Kaposi's sarcoma.

iv) HIV encoded proteins in HIV infected patients.

Thus, the antigens recognised by tumour-reactive CTL can be divided into three main categories: (i) normal self antigens expressed at high levels in tumour cells; (ii) mutated self antigens expressed in tumour cells; (iii) viral antigens expressed in tumours associated with viral infection. Category (i) is preferred.

Three subtypes are included in category (i):

a) normal cellular proteins that are overexpressed;

b) proteins that are expressed in a tissue-specific fashion in normal cells but also in tumours; and c) proteins that are embryonic antigens, silent in most adult tissues but aberrantly expressed in tumours.

Examples of b) and c) are:

b) tissue-specific differentiation antigens as targets for tumour-reactive CTL such as GATA-1, IKAROS, SCL (expressed in the haematopoietic lineage and in leukaemias); and immunoglobulin constant regions (for treatment of multiple myeloma); and c) Wilms-tumour antigen 1 (WT1) for treatment of leukaemias and Wilms tumour and carcinoembryonic antigens (CEA a foetal protein) for liver and intestinal tumours.

Overexpression of oncogene-encoded proteins in human tumours and mutated oncogenes expressed in human tumours are described in Stauss & Dahl (1995) *Tumour Immunology*, Dalgleish/Browning, Chapter 7, incorporated herein by reference.

Thus, it is preferred if the disease to be treated is cancer; more preferably any one of breast cancer; bladder cancer; lung cancer; prostate cancer; thyroid cancer; leukaemias and lymphomas such as CML, ALL, AML, PML; colon cancer; glioma; seminoma; liver cancer; pancreatic cancer; bladder cancer; renal cancer; cervical cancer; testicular cancer; head and neck cancer; ovarian cancer; neuroblastoma and melanoma.

CML is chronic myelocytic leukaemia; ALL is acute lymphoblastic leukaemia; AML is acute myelocytic leukaemia; and PML is pro-myelocytic leukaemia.

The disease to be treated may be any disease caused by a pathogen, particularly a bacterium, yeast, virus, trypanosome and the like. It is preferred if the disease is caused by a chronic infection with a pathogen. It is also preferred if the pathogen is one which is not readily cleared by the host immune system.

It is preferred if the disease is a viral infection; more preferably a disease caused by any one of HIV, papilloma virus, Epstein-Barr virus, HTLV-1, hepatitis B virus, hepatitis C virus, herpes virus or any virus that causes chronic infection. It is particularly preferred if the virus is HIV.

Abnormal glycosylation of polypeptides is also known to occur in some diseases and diseased cells.

Abnormally elevated amounts of a hormone produced by cells occur in some diseases such as certain types of thyroid disease. Thus, the method of the invention is usefully employed to ablate the cells producing the elevated amounts of the hormone. It will be appreciated that, even if the hormone itself, or at least a part thereof, is not presented by an HLA class I (or equivalent) molecule, there may be molecules in the cell which are either abnormal or abnormally elevated and which are presented by an HLA class I (or equivalent) molecule. For example, in certain diseases where a hormone is overproduced by a cell, the biosynthetic enzymes involved in synthesis of said hormone may be overproduced by the cell.

Bacterial infections, particularly those that cause chronic infection may also be usefully treated by-the method of the invention. It is preferred if the bacterial infection is an intracellular infection. Thus, the method may be useful in treating tuberculosis.

The method may also be used to treat malaria.

It is preferred if the HLA class I (or equivalent) molecule type of the patient is determined prior to administration of CTL. This is particularly preferred when the CTL are derived from an individual other than the patient whose HLA class I (or equivalent) molecules are mismatched with those of the patient.

Because of the very extensive study of the genetics of the HLA class I system the type can readily be determined using DNA typing. In particular it is convenient to use a DNA amplification-based typing system such as PCR. These methods are well known in the art and can be employed on a small tissue sample such as a saliva sample or scrape of mouth epithelial cells.

It will be appreciated that the method of the invention may be employed with any mammal such as human, cat, dog, horse, cow, sheep or pig.

It is most preferred if the patient is a human.

Although it is preferred that the patient and the donor of the CTL are the same species, for example both human, it is contemplated that the method is also useful where the patient and the donor are from different species. In other words, the method of the first aspect of the invention includes that a human patient may be given CTL from a non-human donor.

The cytotoxic T lymphocytes for use in the method of the invention, particularly a clonal population of CTL, can conveniently be made using the method of the third aspect of the invention described below.

A particularly preferred embodiment of the first aspect of the invention is wherein the HLA class I (or equivalent) molecule type of the patient is determined prior to administration of the CTL, the CTL are derived from an individual which individual does not carry the HLA class I (or equivalent) molecule type which, in the patient, presents at least part of said abnormal molecule, or molecule abnormally, elevated contained in or associated with the diseased cells of said patient, and the CTL is selected from a library of CTL clones, said library comprising a plurality of CTL clones each derived from an individual with a different HLA class I (or equivalent) molecule type and each said CTL clone recognises said diseased cells.

More preferably each said CTL clone recognises at least part of the same molecule contained in or associated with said diseased cells.

It is preferred if between about $10^8$ and $10^{11}$ CTL are administered to the patient; more preferably between $10^9$ and $10^{10}$ CTL. The cells may be given to a patient who is being treated for the disease by some other method. Thus, although the method of treatment may be used alone it is desirable to use it as an adjuvant therapy.

The CTL may be administered before, during or after the other therapy.

When the disease to be treated is a cancer it is preferable if the cancer has been, is being or will be treated with a conventional therapy or surgery as well as with the method of the invention. Conveniently, depending on the therapy, the cancer is treated by radiotherapy or by chemotherapy.

When the disease to be treated is an infection by a pathogen it is preferable if the infection has been, is being or will be treated with a conventional therapy or surgery.

If the patient to be treated has HIV infection it is preferable if the method of the invention is used as an adjuvant to treatment with a reverse transcriptase inhibitor such as AZT or 3TC.

When the method of the invention is used to treat a solid tumour it is preferred if the CTL are administered as the first post-surgery treatment.

When the method of the invention is used to treat leukaemia it is preferred if the CTL are administered after radiotherapy or chemotherapy. It is also preferred if leukaemia patients are also treated with the CTL in combination with bone marrow transplantation.

The CTL may be administered by any convenient route. It is preferred if the CTL are administered intravenously. It is also preferred if the CTL are administered locally to the site of the disease (such as a tumour or local viral or bacterial infection). Conveniently, the CTL are administered into an artery that supplies the site of the disease or the tissue where the disease is located.

A second aspect of the invention provides use of cytotoxic T lymphocytes (CTL) in the manufacture of a medicament for treating a patient with a disease wherein the patient contains diseased cells which cells contain, or are associated with, an abnormal molecule or an abnormally elevated amount of a molecule and which cells are capable of presenting at least part of said molecule on their surface by an HLA class I (or equivalent) molecule, wherein the cytotoxic T lymphocytes recognise at least part of said molecule when presented by an HLA class I (or equivalent) molecule on the surface of a cell and they are not derived from the patient with a disease.

A third aspect of the invention provides a method of making a clonal population of cytotoxic T lymphocytes (CTL) reactive against a selected molecule the method comprising the step of (a) co-culturing a sample containing CTL, or a precursor thereof, derived from a healthy individual with a stimulator cell which expresses HLA class I (or equivalent) molecules on its surface and that presents at least a part of the selected molecule in a large proportion of occupied said HLA class I (or equivalent) molecules present on the surface of said stimulator cell and (b) selecting a CTL clone reactive against said selected molecule when at least a part of said molecule is presented by an HLA class I (or equivalent) molecule on the surface of a cell.

It will be appreciated that the stimulator cells of the method may be made using the methods described in WO 93/17095, incorporated herein by reference, and it will be appreciated that the method steps of the method are essentially the same as those described in WO 93/17095 with the very important exception that in the present case the method involves co-culturing a sample containing CTL or a precursor thereof derived from a healthy individual with a stimulator cell whereas the method of WO 93/17095 makes use of a source of CTL from a patient to be treated with the cells. In addition, the present invention, in contrast to WO 93/17095, prefers raising CTL against peptides presented by allogeneic not syngeneic HLA class I (or equivalent) molecules.

In particular, the following-portions of WO 93/17095 are incorporated by reference: the "Detailed Description" on pages 23 to page 52, line 11 which describes the production of a stimulator cell; the section on the generation of peptides with optimal binding characteristics for Class I molecules on page 90 onwards; and the Class I molecule bank described on pages 123 and 124.

By "large proportion" we mean at least 50% of the occupied HLA Class I (or equivalent) molecules", more preferably at least 70%, still more preferably at least 90% and most preferably at least 99%".

A "sample containing CTL or a precursor thereof" may be any suitable such sample and specifically includes, but is not limited to, peripheral blood mononuclear cells (PBMC), umbilical cord blood (which is a naive T cell source), any tissue which contains an invasion of T cells and any body fluid which contains T cells or precursors thereof, and includes thymocytes.

The sample containing CTL may or may not be a culture of CTL which have been cloned in vitro.

Preferably, said sample containing CTL or a precursor thereof is PBMC.

Preferably, said molecule is a polypeptide.

Suitably, said selected molecule is an abnormal molecule associated with a diseased cell, or a molecule associated with a diseased cell wherein an abnormally elevated amount of said molecule is present in said diseased cell.

By "molecule associated with a diseased cell" we include any molecule which is found in an abnormal form in the diseased cell or is found in abnormally elevated levels in the diseased cells. Of course, it is most convenient if the said selected molecules, and more particularly the parts thereof presented by the HLA class I (or equivalent) molecules on the stimulator cells, are synthetic equivalents of peptides produced by processing of cellular proteins (which may be intracellular, surface expressed, secreted and so on), and HLA-associated presentation on the cell. Methods are known, particularly computer-based methods using peptide motifs, for selecting a peptide sequence from a larger polypeptide wherein said peptide sequence is a good candidate for binding to a particular HLA class I molecule (or equivalent) type. In particular, it is preferred if said selected molecules are synthesised in vitro. It is particularly preferred if the part of the selected molecule is a peptide and this is made by standard peptide synthetic methods. Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutarine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide 1-hydroxybenzotiazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis, or by MALDI (matrix assisted laser desorption ionisation) mass spectrometry or electrospray mass spectrometry.

Conveniently, said selected molecule is a mutant polypeptide associated with a diseased cell or a polypeptide present at a higher level in said diseased cell compared to a non-diseased cell.

Preferably said diseased cell is any one of a cancer cell, a virus-infected cell, a bacterium-infected cell and a cell expressing an abnormally elevated amount of a hormone.

More preferably the healthy individual is a human. It is also preferred that the CTL are raised against peptides presented by allogeneic not syngeneic HLA class I (or equivalent) molecules.

It is preferred if the polypeptides are any of the following:
i) normal cellular proteins that are expressed at abnormally high levels in tumours; eg cyclin D1 in a variety of tumours; cyclin E in breast cancer; mdm 2 in a variety of tumours; EGF-R, erb-B2, erb-B3, FGF-R, insulin-like growth factor receptor, Met, myc, p53 and BCL-2 are all expressed in various tumours.
ii) normal cellular proteins that are mutated in tumours; eg Ras mutations in a variety of tumours; p53 mutations in a variety of tumours; BCR/ABL translocation in CML and ALL; CSF-1 receptor mutations in AML and MDS; APC mutations in colon cancer; RET mutations in MEN2A, 2B and FMTC; EGFR mutations in gliomas; PML/RARA translocation in PML; E2A-PBX1 translocation in pre B leukaemias and in childhood acute leukaemias.
iii) virally encoded proteins in tumours associated with viral infection; eg human papilloma virus proteins in cervical cancer; Epstein-Barr virus proteins in B cell lymphomas and Hodgkin's lymphoma; HTLV-1 proteins in adult T cell leukaemia; hepatitis B and C virus proteins in hepatoceliular carcinoma; herpes-like virus proteins in Kaposi's sarcoma.
iv) HIV encoded proteins in HIV infected patients.

Three subtypes are included in category (i):
a) normal cellular proteins that are overexpressed;
b) proteins that are expressed in a tissue-specific fashion in normal cells but also in tumours; and
c) proteins that are embryonic antigens, silent in most adult tissues but aberrantly expressed in tumours.

Examples of b) and c) are:
b) tissue-specific differentiation antigens as targets for tumour-reactive CTL such as GATA-1, IKAROS, SCL (expressed in the haematopoietic lineage and in leukaemias); and immunoglobulin constant regions (for treatment of multiple myeloma); and c) Wilms-tumour antigen 1 (WT1) for treatment of leukaemias and Wilms tumour and carcinoembryonic antigens (CEA a foetal protein) for liver and intestinal tumours.

In a particularly preferred embodiment the method leads to the isolation of CTL clones that recognise peptides presented by HLA class I molecules of cancer patients or HIV patients. The CTL are preferably isolated from HLA mismatched, healthy individuals. In particular, it is preferred if the healthy individual does not carry the HLA class I (or equivalent) molecule type which, on the stimulator cell, presents at least a part of the selected molecule. This will ensure that the CTL repertoire of the healthy responder will not be tolerant to the part of the selected molecule presented by the HLA molecule of the patient. This is because of the fact that T cell tolerance is self-HLA restricted. This means that the CTL of a healthy responder individual will be tolerant only to peptide fragments presented by his/her own HLA molecules, but not to peptide fragments presented by mismatched HLA molecules of a patient. Thus, it is preferred if the CTL which are made using this aspect of the invention are allo-restricted and are allogeneic with respect to the patient. Once isolated, the CTL can be used for adoptive immunotherapy of all patients expressing appropriate HLA class I molecules as described in the method of the first aspect of the invention. Conveniently, the method of this third aspect of the invention is used to generate a bank or library of CTL clones recognising peptides derived from tumour associated proteins or HIV proteins presented by different HLA class I molecules. This bank of CTL clones is available for patients expressing the appropriate HLA class I molecules. Thus, adoptive immunotherapy will no longer depend upon the elaborate production of autologous CTL clones for each patient, but will be achieved with 'ready to go' heterologous CTL clones.

The method of this aspect of the invention is particularly suited for the production of CTL against self proteins that are expressed at abnormally high levels in tumours or against self proteins that are expressed in tumours and in a limited number of normal cells (tissue-specific differentiation antigens), or against embryonic antigens whose expression is activated in tamour cells. It is possible that cancer patients are frequently tolerant to self peptides derived from these proteins and cannot mount CTL responses. This is different in HLA mismatched individuals. Their T cell repertoire will not be tolerant to self peptides presented in the context of the class I molecules expressed by HLA mismatched cancer patients. Therefore, using HLA mismatched, healthy individuals, it will be possible to isolate CTL which recognise self peptides presented by class molecules of cancer patients. By definition, such CTL are molecule-specific, usually peptide-specific, and restricted by allogeneic class I molecules. These CTL are expected to efficiently lyse tumour cells presenting these peptides, whilst normal cells do not present these peptides or the levels of presentation are too low to stimulate CTL lysis.

In addition to abnormally expressed self peptides, mutated self peptides derived from mutated oncogenes, or viral peptides derived from HIV also represent targets for adoptive immunotherapy. Thus, in a further preferred embodiment, CTL are generated in vitro from healthy individuals. These CTL are specific for the mutated or viral peptides presented by HLA class I molecules of cancer patients or HIV infected patients. The peptide presenting class I alleles may be shared between the patients and the healthy donors, in which case the in vitro generated CTL will be self HLA-restricted. Alternatively and preferably, patients and healthy donors may be HLA mismatched, in which case the CTL will be allo-restricted. Allo-restricted CTL may be advantageous in situations where the precursor frequency and/or avidity of self-restricted CTL is low.

The method of this aspect of the invention is suitable for generating allo-restricted or self-restricted CTL clones against selected peptides derived from tumour-associated proteins or HIV proteins. The CTL are conveniently generated in vitro by co-culturing PBMC from healthy individuals with stimulator cells that present a tumour-associated or HIV peptide in a large proportion of MHC class I molecules. This facilitates the isolation of CTL clones specific for a complex of selected peptide plus MHC class I molecule expressed by the stimulator cells. Such CTL clones may be useful for adoptive immunotherapy of all patients who express the MHC class I allele against which the CTL have been raised.

The concept of raising allo-restricted, peptide specific CTL is now discussed.

Although the high ligand density model postulates that allo-reactive CTL recognise allogeneic MHC molecules directly, there is currently no conclusive experimental evidence in its support. In contrast, there is good evidence that allo-reactive CTL clones recognise specific peptides presented in the peptide binding groove of allogeneic MHC molecules (8, 9). Therefore, these CTL clones are molecule-specific, usually peptide-specific, and recognition is restricted by allogeneic class I molecules. Nevertheless, the fine specificity of primary CTL responses induced against allogeneic MHC class I molecules is usually unknown. This is because numerous peptides derived from various cellular proteins are presented in the peptide binding groove of MHC class I molecules. Thus, primary allo-restricted CTL responses are inherently poly-specific and directed against numerous MHC bound peptides of unknown sequence. This has previously made it difficult to induce allo-restricted CTL of desired peptide specificity. In addition to this technical difficulty, the possibility of inducing peptide-specific, allo-restricted CTL previously has not been seriously investigated previously because it violates a fundamental immunological concept. The selection of the T cell repertoire takes place in the thymus where two key events occur (10). During negative selection T cells expressing T cell receptors (TCRs) that recognise with high affinity MHC molecules presenting self peptides are deleted from the repertoire. In contrast, TCRs that recognise MHC/peptide complexes with low affinity are positively selected and released into the periphery as mature T cells. It is believed that as a consequence of positive selection the mature T cells are self MHC-restricted. Thus, mature T cells are thought to efficiently recognise immunogenic peptides only when they are presented by self MHC molecules, but not when they are presented by allogeneic MHC molecules.

Here, it is proposed to employ allo-restricted as well as self-restricted CTL from healthy individuals for adoptive immunotherapy. The CTL recognised peptides may be derived from proteins whose expression is activated in tumours, from proteins that are overexpressed in tumours, from tissue-specific proteins that are expressed in tumours, from mutated proteins, or from viral proteins. In experiments described below, we found that it is possible to isolated peptide-specific, allo-restricted CTL. Some allo-restricted CTL clones can recognise very low concentrations of peptides (femtomolar concentrations) indicating that they are at least as sensitive (perhaps even more sensitive) than self-restricted CTL which typically require picomolar peptide concentrations for recognition. We also found that these CTL can be injected three times into immunocompetent hosts without causing any immunological reactions (eg anaphylaxis or hypersensitivity). The allo-restricted CTL clones are probably most efficient for short term treatment of immunocompromised patients. It is unlikely that these CTL will have any long term side effects because they will be eventually eliminated by a functional host immune response.

Allo-restricted CTL may be particularly useful in the treatment of leukaemia. Leukaemia patients, in particular CML patients, are frequently treated by bone marrow transplantation, and there is strong evidence that the disease prognosis is improved when donor CTL can mount an immune response against recipient's leukaemia cells. It is known that donor CTL in bone marrow transplant recipients can mount an immune response against recipient's MHC molecules, leading to the clinical picture of graft versus host disease (GvH). In leukaemia patients a low level of GvH is clinically favourable, since it is correlated with prolonged leukaemia free survival (5). This graft versus leukaemia (GvL) effect is most likely due to donor CTL that can recognise and kill recipients leukaemic cells (6, 7). Whether allo-reactive CTL that mediate GvH and GvL are the same or represent distinct CTL populations has remained a controversial issue. This is because the peptide-specificity of CTL involved in GvH and GvL is generally unknown.

The protocol described here can lead to the isolation of CTL clones which mediate GvL without causing GvH. CTL with specificity for leukaemias can be generated against peptides which are expressed in leukaemic cells but not in cells outside the haematopoietic lineage. Such CTL clones can be used for adoptive immunotherapy of leukaemia patients, where they will eliminate leukaemic cells and perhaps also some normal bone-marrow derived cells. The possible loss of normal bone-marrow cells is not expected to cause any problems because these patients are frequently treated with bone marrow transplantation from healthy donors. The following proteins are some of the targets for anti-leukaemia CTL clones: GATA-1, IKAROS, SCL, WT1. GATA-1 and IKAROS are zinc finger-containing DNA binding proteins expressed only in haematopoietic cells. SCL is a helix-loop-helix transcription factor expressed in haematopoietic cells but also in endothelial cells and brain. Wilms tumour 1 (WT1) protein is an embryonic differentiation antigen not normally expressed in adult tissues except for acute and chronic leukaemias.

Except for SCL, these proteins are expressed in leukaemia progenitor cells but not in cells outside the haematopoietic lineage in adults. Peptides derived from these proteins which are presented by HLA-class I molecules are used to raise CTL from donors who express mismatched HLA class I alleles (to circumvent CTL tolerance), or from donors who express matched class I alleles (in case tolerance is not a problem). CTL clones are isolated and their specificity is analysed against leukaemic cells and non-leukaemic control in vitro. Clones with appropriate specificity are used for treatment of all leukaemia patients expressing the HLA class I allele that is the CTL restriction element.

Similarly, allo-restricted CTL clones are believed to be useful for treatment of patients with multiple myeloma. Suitable targets for multiple myeloma-specific CTL include the constant regions of the immunoglobulin heavy and light chain. Peptides are selected from the heavy and light chain constant regions which bind to HLA class I molecules. CTL against these peptides are isolated from HLA mismatched donors in order to circumvent CTL tolerance. These allo-restricted CTL lyse myeloma cells but also normal B cells in patients treated by adoptive immunotherapy. The eliminated B cells will be replaced by new B cells developing in the patient's bone marrow, whilst elimination of myeloma cells may be permanent.

A particularly preferred embodiment is the generation of allo-restricted CTL against known epitopes in HIV proteins and in tumour-associated proteins. A number of CTL recognised peptides have been identified in various HIV proteins and in tumour-associated proteins. In particular, CTL epitopes have been identified in the HIV env, gag, pol, vif and nef proteins (12, 13). Also, CTL epitopes have been identified in the tumour-associated melanoma proteins tyrosinase, mart1/melanA, gp100/pmel17, mage and bage (14–21). The use of peptides corresponding to these CTL epitopes has the advantage that they are known to be produced by natural antigen processing. CTL produced in this way recognise target cells expressing the relevant proteins endogenously. The exploitation of known CTL epitopes represents a considerable shortcut because it avoids screening of large numbers of test peptides and identification of naturally produced peptides. However, known peptides may represent immunodominant peptides. The method of the third aspect of the invention may be used to identify new peptides, which new peptides may be preferred as they are likely to be subdominant peptides. Since subdominant peptides are less likely to be immunoselected by patient's CTL responses, they may represent better targets for adoptive immunotherapy. Nevertheless, peptides representing known CTL epitopes can be ideally exploited to generate allo-restricted or self-restricted CTL in vitro and to test their anti-viral and anti-tumour effects in vivo.

The method of the third aspect of the invention allows the isolation of HLA class I-restricted CTL clones specific for peptides produced in tumour cells and for peptides produced in HIV infected cells. Conveniently, SCID mouse models are used to determine the in vivo antitumour and anti-HIV effects of these CTL. These CTL clones are useful for adoptive immunotherapy, especially in humans.

It is preferred if the method of the third aspect of the invention further comprises determining the HLA class I (or equivalent) molecule type of the healthy individual. Conveniently, this is done by DNA analysis as disclosed above.

It is particularly preferred if the stimulator cell has a type of HLA class I (or equivalent) molecule on its surface which HLA class I (or equivalent) molecule type is not present in the healthy individual.

It is particularly preferred if said stimulator cell is a cell which is substantially incapable of itself loading said HLA class I (or equivalent) molecule with at least a part of said selected molecule. As is described in more detail below, the HLA class I (or equivalent) molecule may readily be loaded with at least a part of said selected molecule in vitro.

Conveniently, said cell is a mammalian cell defective in the expression of a peptide transporter such that, when at least part of said selected molecule is a peptide, it is not loaded into said HLA class I (or equivalent) molecule.

Preferably the mammalian cell lacks or has a reduced level or has reduced function of the TAP peptide transporter. Suitable cells which lack the TAP peptide transporter include T2, RMA-S and Drosophila cells. TAP is the Transporter Associated with antigen Processing.

Thus, conveniently the cell is an insect cell such as a Drosophila cell.

The human peptide loading deficient cell line T2 is available from the American Type Culture Collection, 12301

Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Karre and Ljunggren (1985) *J. Exp. Med.* 162, 1745, incorporated herein by reference.

In a preferred embodiment the stimulator cell is a host cell (such as a T2, RMA-S or Drosophila cell) transfected with a nucleic acid molecule capable of expressing said HLA class I (or equivalent) molecule. Although T2 and RMA-S cells do express before transfection HLA class I molecules they are not loaded with a peptide.

Mammalian cells can be transfected by methods well known in the art. Drosophila cells can be transfected, as described in Jackson et al (1992) *Proc. Natl. Acad. Sci. USA* 89, 12117, incorporated herein by reference.

Conveniently said host cell before transfection expresses substantially no HLA class I (or equivalent) molecules.

It is also preferred if the stimulator cell expresses a molecule important for T cell costimulation such as any of B7.1, B7.2, ICAM-1 and LEA 3.

The nucleic acid sequences of numerous HLA class I (and equivalent) molecules, and of the costimulator molecules, are publicly available from the GenBank and EMBL databases.

It is particularly preferred if substantially all said HLA class I (or equivalent) molecules expressed in the surface of said stimulator cell are of the same type.

HLA class I in humans, and equivalent systems in other animals, are genetically very complex. For example, there are at least 110 alleles of the HLA-B locus and at least 90 alleles of the HLA-A locus. Although any HLA class I (or equivalent) molecule is useful in this aspect of the invention, it is preferred if the stimulator cell presents at least part of the selected molecule in an HLA class I molecule which occurs at a reasonably high frequency in the human population. It is well known that the frequency of HLA class I alleles varies between different ethnic groupings such as Caucasian, African, Chinese and so on. At least as far as the Caucasian population is concerned it is preferred that HLA class I molecule is encoded by an HLA-0201 allele, or an HLA-A1 allele or an HLA-A3 allele or an HLA-B7 allele. HLA-A0201 is particularly preferred.

When the method of the third aspect of the invention is used to make a library of CTL it is convenient if the HLA alleles which restrict recognition by those CTL clones are selected on the basis of frequency in a particular ethnic grouping.

It will be appreciated that a stimulator cell which expresses HLA class I (or equivalent) molecules on its surface and that presents at least a part of a selected molecule in a large proportion of occupied said HLA class I (or equivalent) molecules present on the surface of said stimulator cell forms a further aspect of the invention.

Preferably the selected molecule is an abnormal molecule or a molecule whose amount is abnormally elevated.

A fourth aspect of the invention provides a clonal population of cytotoxic T lymphocytes reactive against a selected molecule obtainable by the method of the third aspect of the invention.

A fifth aspect of the invention provides a clonal population of cytotoxic T lymphocytes reactive against a selected molecule wherein the said CTL has a high avidity for a cell.

It will be appreciated that, at least for self molecules abnormally elevated, and in particular for self polypeptides expressed at high levels, the method of the third aspect of the invention allows the production of CTL of much higher avidity and sensitivity than can otherwise be produced. This is particularly the case when the stimulator cell has a type of HLA class I (or equivalent) molecule on its surface which HLA class I (or equivalent) molecule type is not present in the healthy individual.

Thus, the method of the third aspect of the invention is preferably used to produce cytotoxic T lymphocytes (CTL) from healthy individuals that can be used for adoptive immunotherapy of cancer patients and patients infected with the human immunodeficiency virus. The CTL are generated entirely in vitro and may be administered to patients intravenously. Since this form of adoptive immunotherapy does not depend upon a functional host immune system, it is believed to be particularly suited to patients who are immunosuppressed, for example as a consequence of HIV infection or radiotherapy and chemotherapy in the case of cancer. Preferably, all peptide-specific CTL are isolated from healthy donors, and no blood samples from patients are required.

The hallmark of the allo-restricted CTL clones described herein is that they can recognise peptides derived from normal cellular proteins presented on the cell surface by MHC class I molecules. Most importantly, the MHC genotype of the allo-restricted CTL clones and of the recognised target cells (or other cells) in the patient is different. The genetic difference does not only apply to the MHC region of the genome, but also to other polymorphic genes. Thus, it is possible that there might be a polymorphism in the gene segments of the TCR$\alpha$ and $\beta$ locus of the CTL clone and the target cell. However, the TCR genes in these cells may be identical even if CTL and target cell are of different genetic origin.

A sixth aspect of the invention provides a clonal population of cytotoxic T lymphocytes according to the fourth or fifth aspects of the invention for use in medicine.

A seventh aspect of the invention provides a pharmaceutical composition comprising clonal population of cytotoxic T lymphocytes according to the fourth or fifth aspects of the invention and a pharmaceutically acceptable carrier.

The aforementioned CTL of the invention or a formulation thereof may be administered by any conventional method including by parenteral (eg subcutaneous or intramuscular) injection. The treatment may consist of a single dose or a plurality of doses over a period of time.

Whilst it is possible for the CTL of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

An eighth aspect of the invention provides use of a clonal population of cytotoxic T lymphocytes derived from a healthy individual and reactive against a selected abnormal molecule derived from a diseased cell from a patient with a disease, or a selected molecule derived from a diseased cell from a patient with a disease wherein an abnormally elevated amount of said molecule is present in said diseased cell, in the manufacture of a medicament for treating a patient with the disease wherein said healthy individual has a different HLA type to said patient.

A ninth aspect of the invention provides a library of CTL clones, said library comprising a plurality of CTL clones derived from individuals and each said CTL clone is restricted by a different HLA class I allele and recognises a molecule associated with a selected disease.

The library is conveniently stored in a form where each CTL clone retains viability. Conveniently the library is stored frozen.

Preferably, the library contains a selection of CTLs which have been made by the method of the third aspect of the invention. The library may be disease or disease cell specific or it may be HLA class I (or equivalent) molecule type specific. Preferred diseases or HLA class I (or equivalent) molecule types are described above.

Advantageously the library contains CTL for different diseases and/or CTL for different molecules (eg peptides) for the same disease and clones of each of the CTL are restricted by different HLA class I alleles. For an individual patient an appropriate CTL clone is selected by reference to an appropriate peptide (ie one that is presented on their disease cells), and by reference to the HLA class I allele of the CTL such that the CTL bears an HLA class I allele different from that of the patient.

A tenth aspect of the invention provides a therapeutic system comprising (a) means to determine the HLA class I (or equivalent) type of a patient to be treated and (b) a library of CTL clones, said library comprising a plurality of CTL clones derived from individuals with differing HLA class I (or equivalent) molecule type and each said CTL clone recognises a molecule associated with a selected disease.

The method of treating a patient according to a particular embodiment of the first aspect of the invention makes use of allogeneic CTL which are particularly suited for use in adoptive immunotherapy when the antigen recognised is a self-antigen.

However, because of their allogeneic nature, the recipients (patients) are expected to mount immune responses against the transferred CTL in some circumstances, which may limit their half life and their anti-tumour activity in the recipient host (patient). However, immunosuppression of the recipient (patient) is one way of diminishing such host immune responses and the method of the first aspect of the invention is useful.

The other possibility described here is to use autologous CTL which are non-immunogenic when transferred back into the original host. These autologous CTL are manipulated in vitro to express the TCRs isolated from allo-restricted CTL clones.

An eleventh aspect of the invention provides a method of making a cytotoxic T lymphocyte (CTL) suitable for treating a patient, the method comprising (a) making a clonal population of CTL by the method of the third aspect of the invention; (b) preparing a genetic construct capable of expressing the T-cell receptor (TCR) of the said clonal population of CTL, or a functionally equivalent molecule; and (c) introducing said genetic construct into a CTL or precursor thereof which CTL or precursor is derived from said patient.

All of the preferred embodiments of the third aspect of the invention are preferred in this aspect of the invention when making a clonal population of CTL in step (a) of this method. In particular, the CTL isolated in step (a) are preferably isolated from HLA mismatched, healthy individuals (compared to the patient to be treated). Thus, it is particularly preferred if the CTL isolated in step (a) are allo-restricted and are allogeneic with respect to the patient to be treated.

Allogenicity is the situation of two or more different allelic forms of the same protein in different individuals of the same species.

By a "molecule functionally equivalent to a T-cell receptor" we mean any molecule which can perform the same function as a T-cell receptor. In particular, such molecules include genetically engineered three-domain single-chain T-cell receptors as made by the method described by Chung et al (1994) *Proc. Natl. Acad. Sci. USA* 91, 12654–12658, incorporated herein by reference.

By a "genetic construct capable of expressing the T-cell receptor or functionally equivalent molecule" we include any genetic construct, whether RNA or DNA, which, when inserted into the CTL derived from the patient or a precursor of said cell, can express the T-cell receptor or functionally equivalent molecule. Any suitable vector may be used such as a plasmid or virus, including retrovirus.

The genetic construct may be made using methods well known in the art such as those described in Sambrook et al (1989) "Molecular cloning, a laboratory manual", 2nd edition, Cold Spring Harbor Laboratory Press, Cold Spring Harbor, N.Y., incorporated herein by reference.

The DNA encoding the TCR or functionally equivalent molecule may be joined to a wide variety of other DNA sequences for introduction into an appropriate host (which may be the CTL derived from the patient, or a precursor thereof, or another host cell). The companion DNA will depend upon the nature of the host, the manner of the introduction of the DNA into the host, and whether episomal maintenance or integration is desired.

Generally, the DNA is inserted into an expression vector, such as a plasmid or virus or retrovirus, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through known techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to cotransform the desired host cell. However, in the case of introducing the genetic construct into the CTL of the patient, or a precursor thereof, it is preferred if at least 50% of the CTL are transformed or transfected with the genetic construct. More preferably, at least 70% are so transformed or transfected and still more preferably at least 90% or at least 95%.

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA is to use the polymerase chain reaction as disclosed by Saiki et al (1988) *Science* 239, 487–491.

In this method the DNA to be enzymatically amplified is flanked by two specific oligonucleotide primers which themselves become incorporated into the-amplified DNA. The said specific primers may contain restriction endonuclease recognition sites which can be used for cloning into expression vectors using methods known in the art.

A particularly preferred method is now described.

The TCRs of allo-restricted CTL clones specific for self peptides presented at elevated levels in tumours are cloned. The TCR usage in allo-restricted CTL clones is determined using (i) TCR variable region-specific monoclonal antibodies and (ii) RT-PCR with primers specific for Vα and Vβ gene families. A cDNA library is prepared from poly-A mRNA extracted from allo restricted CTL clones. Primers specific for the C-terminal portion of the TCR α and β chains and for the N-terminal portion of the identified Vα and β segments are used. The complete cDNA for the TCR α and β chain is amplified with a high fidelity DNA polymerase and the amplified products cloned into a suitable cloning vector. The cloned α and β chain genes are assembled into a single chain TCR by the method as described by Chung et al (1994) *Proc. Natl. Acad. Sci. USA* 91, 12654–12658. In this single chain construct the VαJ segment is followed by the VβDJ segment, followed by the Cβ segment followed by the transmembrane and cytoplasmic segment of the CD3 ζ chain. This single chain TCR is then inserted into a retroviral expression vector (a panel of vectors may be used based on their ability to infect mature human CD8$^+$ T lymphocytes and to mediate gene expression: the retroviral vector system Kat is one preferred possibility (see Finer et al (1994) *Blood* 83, 43). High titre amphotrophic retrovirus are used to infect purified CD8$^+$ T lymphocytes isolated from the peripheral blood of tumour patients following a protocol published by Roberts et al (1994) *Blood* 84, 2878–2889, incorporated herein by reference. Anti-CD3 antibodies are used to trigger proliferation of purified CD8$^+$ T cells, which facilitates retroviral integration and stable expression of single chain TCRs. The efficiency of retroviral transduction is determined by staining of infected CD8$^+$ T cells with antibodies specific for the single chain TCR. In vitro analysis of transduced CD8$^+$ T cells establishes that they display the same tumour-specific killing as seen with the allo-restricted CTL clone from which the TCR chains were originally cloned. Populations of transduced CD8$^+$ T cells with the expected specificity will be used for adoptive immunotherapy of the tumour patients. Patients will be treated with in between $10^8$ to $10^{11}$ (most likely $10^9$–$10^{10}$) autologous, transduced CTL.

Other suitable systems for introducing genes into CTL are described in Moritz et al (1994) *Proc. Natl. Acad. Sci. USA* 91, 4318–4322, incorporated herein by reference. Eshhar et al (1993) *Proc. Natl. Acad. Sci. USA* 90, 720–724 and Hwu et al (1993) *J. Exp. Med.* 178, 361–366 also describe the transfection of CTL.

Thus, a twelfth aspect of the invention provides a cytotoxic T lymphocyte suitable for treating a patient obtainable by the method of the eleventh aspect of the invention.

A thirteenth aspect of the invention provides a method of treating a patient with a disease wherein the patient contains diseased cells which cells contain, or are associated with, an abnormal molecule or an abnormally elevated amount of a molecule and which cells are capable of presenting at least part of said molecule on their surface by an HLA class I (or equivalent) molecule, the method comprising administering to the patient a therapeutically effective amount of cytotoxic T lymphocytes (CTL) which recognise at least part of said molecule when presented by an HLA class I (or equivalent) molecule on the surface of a cell wherein the CTL is a CTL according to the twelfth aspect of the invention.

A fourteenth aspect of the invention provides the use of cytotoxic T lymphocytes in the manufacture of a medicament for treating a patient with a disease wherein the patient contains diseased cells which cells contain, or are associated with, an abnormal molecule or an abnormally elevated amount of a molecule and are capable of presenting at least part of said molecule on their surface by an HLA class I (or equivalent) molecule, wherein the cytotoxic T lymphocytes recognise at least part of said molecule when presented by an HLA class I (or equivalent) molecule on the surface of a cell and wherein the CTL is a CTL according to the twelfth aspect of the invention.

The preferred methods of administration, the preferred diseases, and the preferred amounts of CTL administered to treat are the same for the thirteenth aspect of the invention as for the first aspect of the invention.

It will be appreciated that a genetic construct and a library of genetic constructs may be prepared, each capable of expressing a specific TCR, or a functionally equivalent molecule, by making clonal populations of CTL by the method of the third aspect of the invention and preparing a genetic construct capable of expressing the T-cell receptor of the said clonal population of CTL, or a functionally equivalent molecule as described above.

It is particularly convenient if each genetic construct represents a TCR (by way of a TCR or a functionally equivalent molecule) which corresponds to the TCR from a particular CTL from a healthy individual of a known HLA genotype and which CTL was produced by co-culturing with a stimulator cell which expresses a known HLA class I (or equivalent) molecule on its surface which HLA class I or equivalent molecule binds at least a part of a given molecule on its surface.

In this way it is possible to generate libraries of genetic constructs each construct of which can be introduced into a patient's CTL or precursor and which genetic construct capable of expressing a TCR or functionally equivalent molecule can be selected on the basis of the patient's HLA genotype and disease to be treated. The particular genetic construct representing a TCR is selected on the basis of the specificity of the T cell clone (ie according to what is expressed by the patient's disease cell, especially a tumour cell).

Preferably, the HLA genotype of the patient and the HLA genotype of the CTL from which the TCR or functionally equivalent molecule expressed by the genetic construct is derived are mismatched.

In general, it is easy to define a TCR as allo-restricted as long as it is expressed in the original CTL clone. However, once the TCR genes are isolated and transferred into patients CTL, it becomes very difficult to define them as allo-restricted. A sequence comparison between the sequence of the transferred TCR and the endogenous TCR genes can identify them as a non-self TCR genes in those cases where there is a polymorphism in the TCR genes. Non-self TCRs are, however, not necessarily derived from allo-restricted CTL clones.

The invention will now be described in more detail with reference to the following Examples and Figures wherein:

BRIEF DESCRIPTION OF THE FIGURES

FIG. 1 shows the results of an experiment where mice were injected with $5\times10^5$ RMA tumour cells only or with tumour cells and $5\times10^5$ CTL. The tumour volume was measured every day. After 11 days mice that received tumour cells only were killed because of tumour ulceration or because of large tumour burden. None of the mice that received CTL had detectable tumours at day 11.

FIG. 2 shows the results of an experiment where mice were injected with $5\times10^5$ RMA cells at day −7 (minus seven) treated with $10^7$ anti-mdm100 CTL i.v. The tumour volume was measured at day 0 and each subsequent day. The relative increase in tumour volume is shown. Mice were killed when tumours ulcerated or reached more than 3 cm$^3$ in volume.

FIG. 3A shows recognition of peptide-coated T2-K$^b$ cells by 6 CTL clones specific for the mdm100 peptide. In total 33 CTL clones were analysed and the peptide titration curves for 16 were similar to that of the clones 3F3F, 1F1H and 3F10A, whilst 17 clones showed titration curves similar to that of the clones 3B11C, 6A6G and 6A6D. FIGS. 3B and 3C show lysis of RMA cells (open diamonds) and RMA-S cells coated with either mdm100 peptides (filled circles) or with class I binding control peptides (open circles) by a representative low "avidity" CTL clone 6A6G FIG. 3B or by a representative high "avidity" clone 3F3F FIG. 3C. FIG. 3D shows lysis of dendritic cells coated with either mdm100 peptides (filled squares) or with class I binding control peptides (open squares) by high avidity clone 3F11A.

Figure 4A:
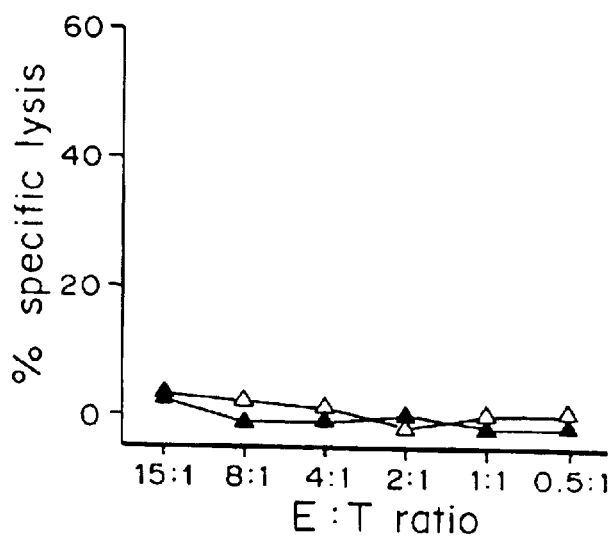
FIGS. 4A and 4B show the recognition of B16 melanoma cells by high "avidity" mdm100-specific CTL.

A representative high avidity CTL clone (1F7E) was analysed in a 4 hour $^{51}$Cr-release assay against the non-metastatic B16-F1 melanoma variant FIG. 4A and against the metastatic variant B16-FF1 and B16-F10 cells were either coated with mdm100 peptides (open symbols) or with MHC class I binding control peptides (solid symbols). Staining experiments revealed that B16-F1 cells were H-2K$^b$ negative and that B16-F10 cells expressed low levels H-2K$^b$ (not shown).

Figure 5A:
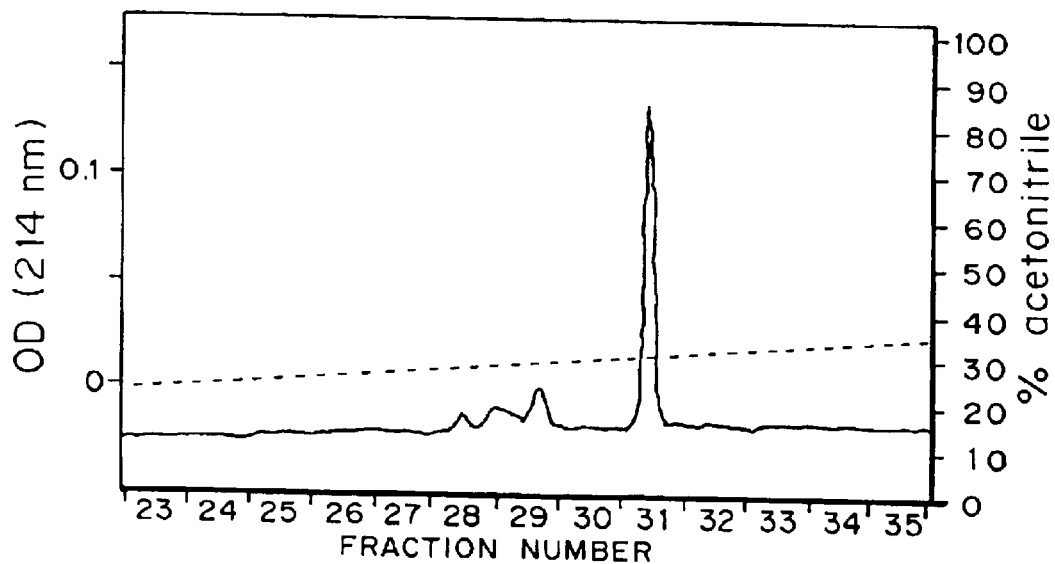
Figure 5B:
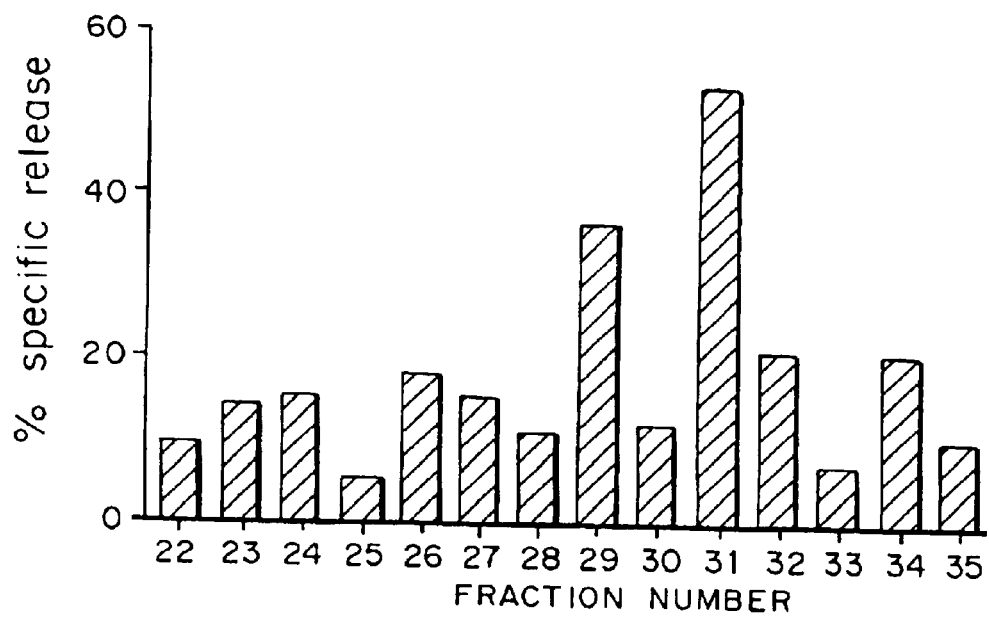

FIGS. 5A and 5B show CTL recognition of naturally produced peptides extracted from RMA lymphoma cells.

FIG. 5A shows HPLC elution profile of 1 μg of the synthetic peptide mdm100. FIG. 5B shows the CTL recognition profile of HPLC fractions containing naturally produced peptides extracted from RMA cells. Peptides were prepared from RMA lymphoma cells as described in Materials and Methods of Example 1, and separated by HPLC using the same conditions as in (A).

Figure 6A:
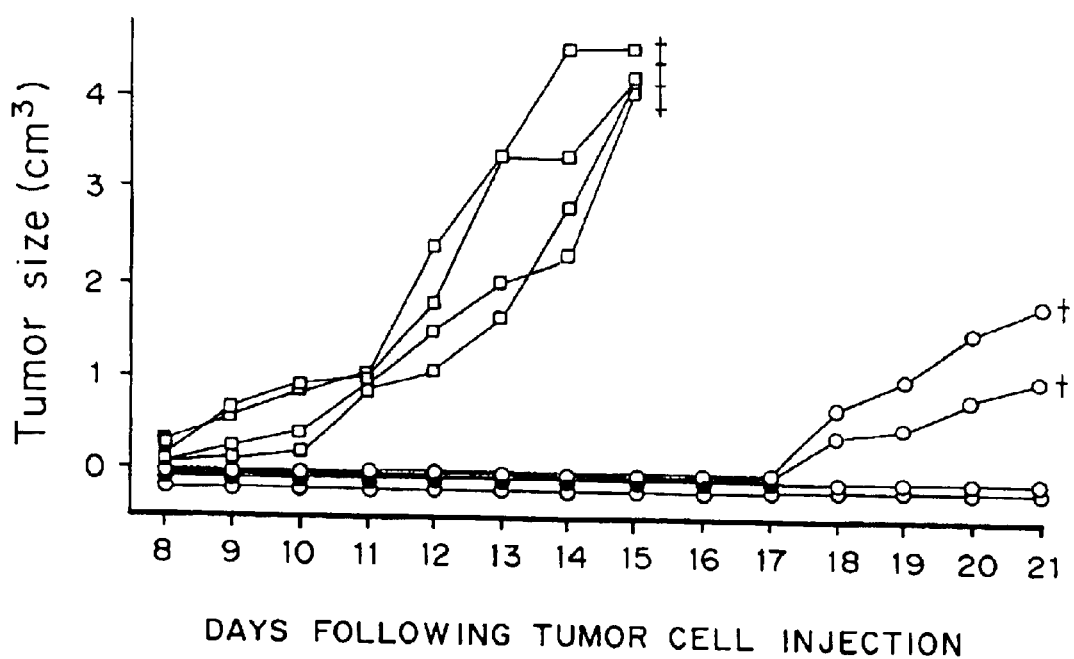
Figure 6B:
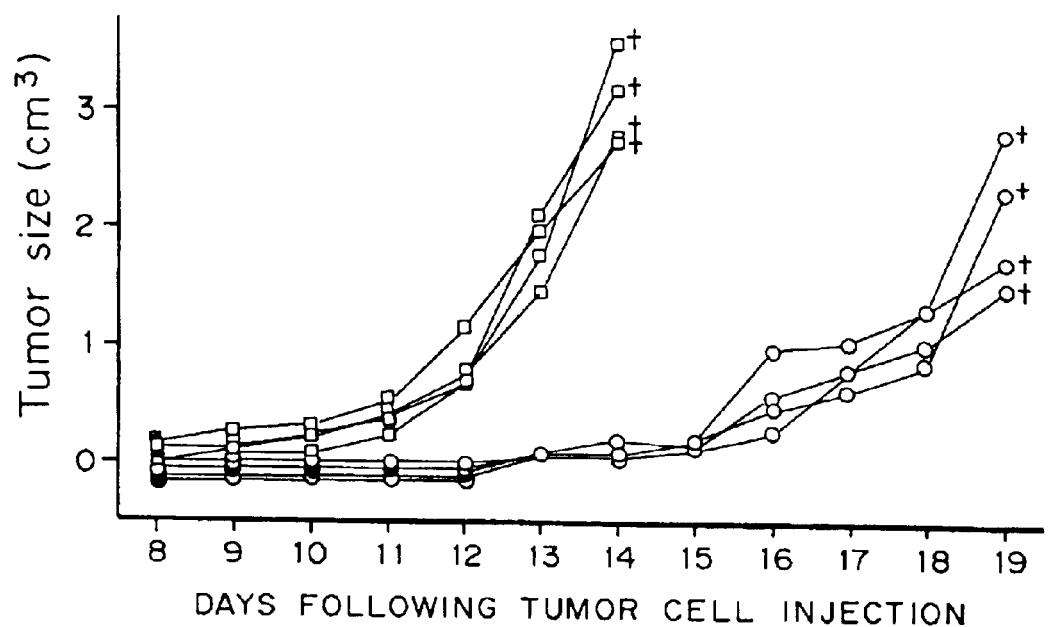
Figure 6C:
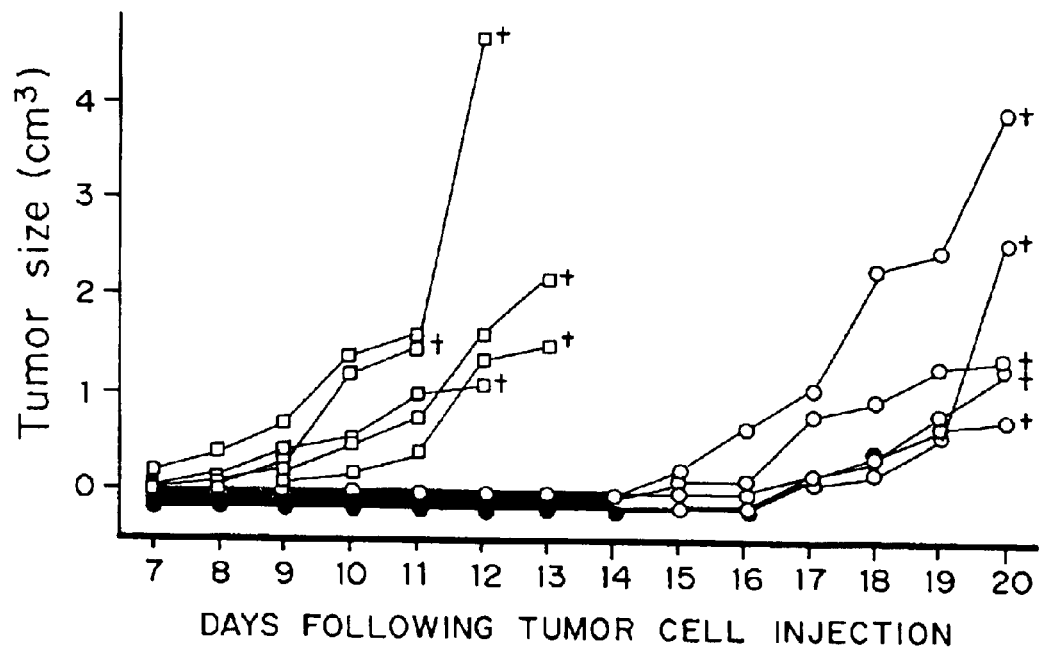

FIGS. 6A, 6B, and 6C shows the control of tumor growth by high avidity, mdm100-specific CTL. For FIG. 6A eight C57BL/10 mice were injected subcutaneously with $10^5$ RMA lymphoma cells (open squares) or with $10^5$ lymphoma cells together with $10^6$ CTL (open circles). For FIG. 6B eight C57BL/10 mice were similarly injected with $5\times10^5$ RMA lymphoma cells (open squares) or with $5\times10^5$ lymphoma cells together with $5\times10^5$ CTL (open circles). For FIG. 6C ten C57BL/6 mice were injected with either $10^5$ B16-F10 melanoma cells (open squares), or with $10^5$ B16-F10 cells together with $10^6$ CTL (open circles). Similar results were obtained when either individual high avidity CTL clones or a mixture of clones were used for these experiments. Mice were monitored daily and the tumor growth for each individual mouse is shown. The crosses indicate that the mice died or were sacrificed because of large tumor burden.

Figure 7A:
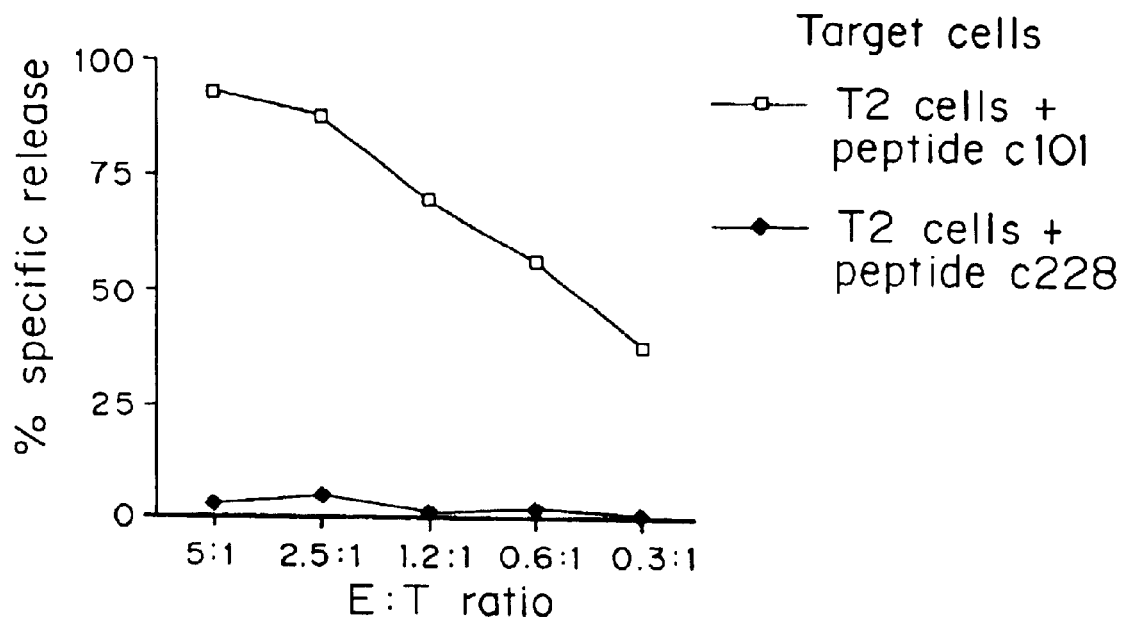
Figure 7B:
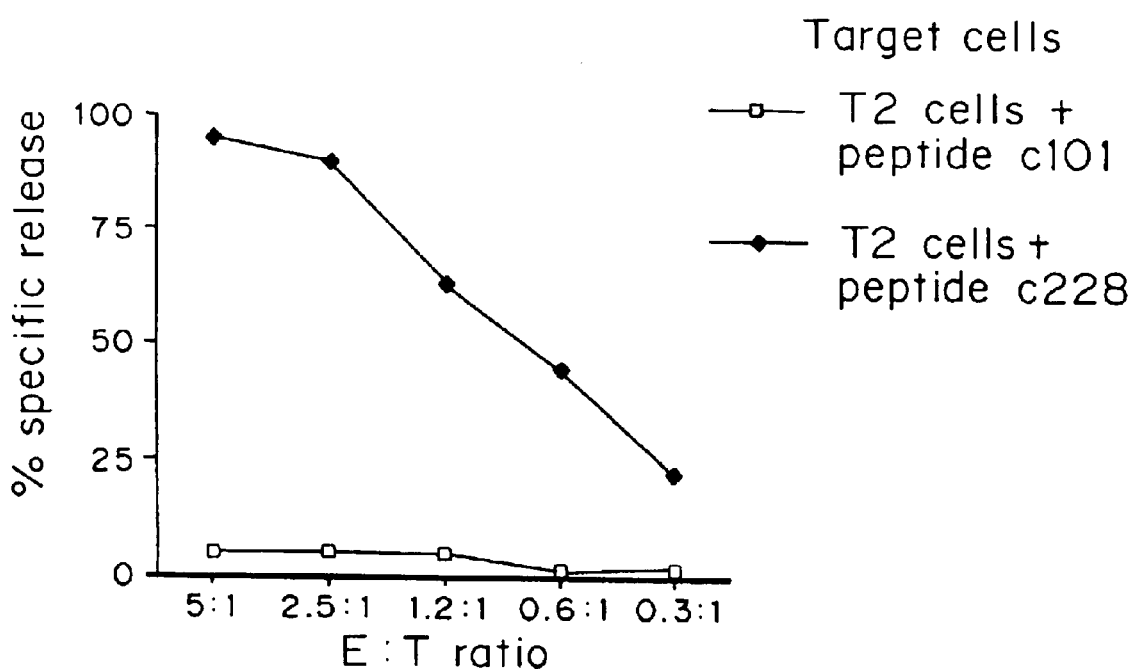

FIG. 7(A) shows the lysis by a CTL clone specific for a HLA-A0201-binding cyclin D1 peptide (101–110). The CTL clone was obtained from HLA-A2 negative PBMC. FIG. 7(B) shows the lysis by a CTL clone specific for a HLA-A0201-binding cyclin D1 peptide (228–234). The CTL clone was obtained from HLA-A2 negative PBMC.

EXAMPLE 1

Adoptive Immunotherapy Using CTL in Mice

SUMMARY

In a murine model system we have generated allo-restricted CTL clones against peptides derived from the normal self protein mdm 2 which is frequently overexpressed in tumours. The CTL kill tumour cells in vitro, whilst normal cells are not recognised. When adoptively transferred into mice, these CTL show anti-tumour effects in vivo.

The two mouse strains C57BL/10 (H-2$^b$) and BALBIc (H-2$^d$) are MHC mismatched and therefore express distinct class I molecules. This MHC mismatch was chosen because it mimics the HLA mismatch found in the human situation, ie the difference between a cancer patient and a healthy T cell donor. We used these two mouse strains to test whether allo-restricted CTL against the murine mdm 2 protein can be detected. The mdm 2 protein can associate with p53 and regulate its biological activity. It is frequently overexpressed in human cancers and consequently represents a possible target for adoptive immunotherapy.

In the murine model system described above, we explored the following questions:

(i) Is it possible to isolate mdm 2 peptide-specific, H-2K$^b$-restricted CTL from BALBIc mice (H-2$^d$ haplotype)?

(ii) Can the BALB/c derived peptide-specific, allo-restricted CTL recognise tumour cells expressing K$^b$ class I molecules?

(iii) Can the BALB/c derived peptide-specific, allo-restricted CTL be used for adoptive tumour immunotherapy in C57BLI/10 mice (H-2$^b$ haplotype)?

We have obtained the following results:

(i) CTL that are specific for an mdm 2 peptide presented by the allogeneic H-2K$^b$ class I molecule were isolated.

(ii) CTL clones were established and shown to kill RMA thymoma cells of H-2$^b$ origin. RMA cells are highly tumourigenic in C57BL/10 mice (H-2$^b$) which allowed us to test whether BALB/c derived CTL might have anti-tumour effects in C57BL/10 hosts.

(iii) In one experiment 8 mice were injected s.c. with $5\times10^5$ RMA cells. 4 of these mice were also injected with $5\times10^5$ CTL. After 11 days, the 4 mice that had been injected with RMA cells alone, had large tumours and were therefore killed, whilst the 4 mice that had received RMA and CTL were tumour free (FIG. 1). In another experiment, 8 mice were injected s.c. with 5×10⁵ tumour cells. After 7 days, when all the mice had developed tumours at the site of injection, 2 of them were treated i.v. with $10^7$ BALB/c derived CTL. In the untreated mice the tumour volume increased rapidly, whilst in those that received CTL, the tumour growth was delayed (FIG. 2).

These results show that this adoptive immunotherapy approach using cytotoxic T cells is effective.

The following provides further details:

Methods

Animals: C57BL/6 mice (H-$2^b$) and BALBIc (H-$d^d$) mice were supplied by the breeding colony of the Royal Postgraduate Medical School, Hammersmith Hospital, London, although this type of mice is readily available from various commercial suppliers. Mice were used at the age of 8 to 10 weeks.

Peptides: The mdm100 peptide corresponds to amino acid 100–107 (YAMIYRNL; SEQ ID No 1) of the murine mdm-2 protein. It has been shown that this peptide bound efficiently to H-$2K^b$ class I molecules. Other peptides derived from mdm-2 or cyclin-D1 that were found to bind to H-$2K^b$ or $D^b$ class I molecules served as controls. All peptides used in this study were synthesised by the central peptide synthesis laboratory of the Imperial Cancer Research Fund, London, using finoc chemistry. The quality of the peptides were assessed by HPLC analysis and the expected molecular weight was observed using MALDI mass-spectrometry. The peptides were dissolved in phosphate buffered saline (pH 7.4) to give a concentration of 2 mM and stored at −20° C.

Cell lines: RMA cells (H-$2^b$) originated from a Rauscher virus-induced C57BL/6N T cell lymphoma. RMA-S cells were derived from RMA cells after mutagenesis with ethyl-methane-sulfonate followed by five rounds of selection with anti-H-2 alloantisera and rabbit complement treatment to obtain cells with decreased levels of MHC class I expression (Ljunggren & Kärre (1985) *J. Exp. Med.* 162, 1745–1759. RMA-S cells were found to have a point mutation at nucleotide 97 of the TAP2 gene, which generates a premature stop codon (Yang et al (1992) *J. Immunol.* 267, 11669–11672). B16-F1 and B16-F10 are variants of the C57BL/6 derived melanoma cell line B16, with low and high metastatic potential, respectively (Fidler & Nicolson (1976) *J. Nati. Cancer Inst.* 57, 1199–1202). The human cell line T2 is a fusion hybrid of a B-lymphoblastoid cell line and a T-lymphoblastoid cell. These cells have no TAP transporter genes and express reduced levels of HLA-A2 and no detectable endogenous HLA-B5 (Alexander et al (1989) *Immunogenetics* 29, 380–88). T2 cells transfected with murine H-$2K^b$ expressed $K^b$ class I molecules at levels that were similar to the levels of HLA-A2. The T2-$K^b$ cells were a gift from Dr T Elliott (John Radcliffe Hospital, Oxford).

CTL induction: Allo-restricted CTL were generated by in vitro stimulation of native BALB/c splenocytes with peptide coated RMA-S and T2-$K^b$ stimulator cells. 4×10⁶ BALB/c splenocytes were stimulated in 24 well plates with 4×10⁵ RMA-S cells coated with mdm100 peptide in complete RPMI media containing 10% FCS and 500 nM peptide. After 5 days, CTL were seeded in 96 well plates at 10, 100 and 1000 responder CTL per well. Each well contained 3×10⁵ irradiated BALBIc splenocytes as feeders, and 10⁴ irradiated T2-$K^b$ stimulator cells that were previously pulsed with mdm100 peptides. The culture media was the same as above, except that recombinant IL-2 was added at a concentration of 10 U/ml. Fresh medium containing feeders and stimulator cells were added after 14 days, and after an additional 5 days each 96 well was tested in a CTL assay against mdm100 coated target cells and control targets. Microcultures that showed mdm100-specific killing were expanded and used for limiting dilution cloning on 96 well plates using 0.1, 1 and 10 CTL per well, 10⁵ BALB/c splenocytes as feeders and 10⁴ T2-$K^b$ stimulator cells. CTL clones were expanded and used in the described experiments.

CTL assays: Cytotdxic activity was determined in 4 hour $^{51}$Cr-release assays against target cells coated with mdm100 peptides or MHC class I-binding control peptides as described (Sadovnikova et al (1993) *Int. Immunol.* 6, 289–296). In some experiments dendritic cells were used as CTL targets. They were prepared from C57BL/10 splenocytes after removal of plastic adherent cells and centrifugation on a layer of 14.5% (w/v) metrizamide as described (Macatonia et al (1989) *J. Exp. Med.* 169, 1255–1264).

Isolation of natural peptides and HPLC separation: 4×10⁸ RMA lymphoma cells were lysed in 4 ml of 2% TFA in $H_2O$. The suspension was homogenised by ultrasonication and cell debris was removed by centrifugation in a centrifuge (Sigma 2K15) at approximately 27000 g for 1 h at 4° C. The supernatant was then transferred into centricon 10 filter nits (Amicon), which were spun at 5000 g for 2.5 h at 4° C. The filtrate containing peptides less than 10 kDa was HPLC separated over a Superpac PepS column (Pharmacia) using as buffer A 0.1% TFA in $H_2O$ and as buffer B 0.1% TFA in acetonitrile. The flow rate was 1 ml/min and the concentration of buffer B was increased from 0% to 60% at 1% per minute. 1 ml fractions were collected, dried in a Servant speedvacuum drier and resuspended in 100 μl PBS. 10 μl of each HPLC fraction were used to coat $^{51}$Cr labelled T2-$K^b$ cells, which then served as targets for mdm100 peptide-specific CTL.

Results

Figure 3A:
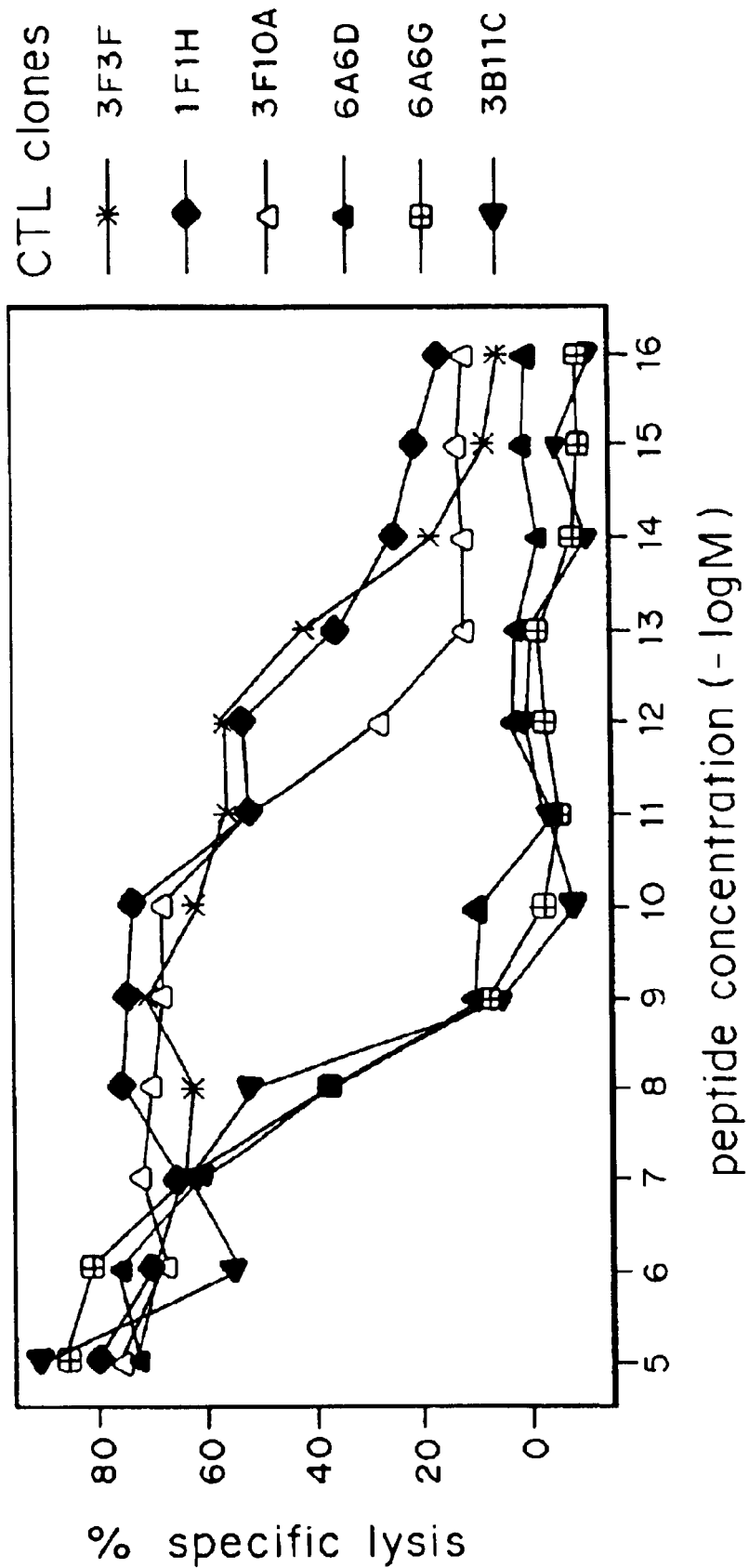
FIGS. 3A, 3B, 3C, and 3D shows the characterisation of allo-restricted CTL clones specific for the mdm100 peptide.
Figure 3B:
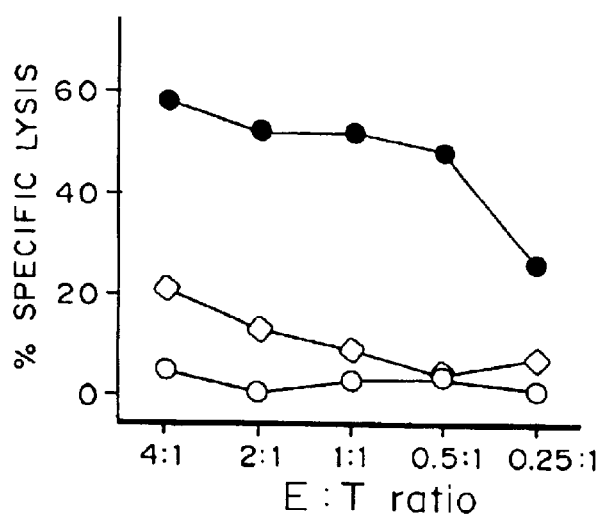

Isolation of high avidity CTL from the allo-restricted repertoire: An mdm-2 derived peptide (mdm100) that efficiently bound to H-$2K^b$ class I molecules has been identified. However, in C57BL/6 mice (H-$2^b$) this peptide only stimulated low avidity CTL that recognised target cells coated with the synthetic mdm100 peptide, but not target cells expressing mdm-2 endogenously. One possible explanation was that high avidity CTL that can recognise low concentrations of naturally produced peptides were deleted from the repertoire of H-$2^b$ mice. Since tolerance is MHC-restricted, the CTL repertoire of BALB/c mice (H-$2^d$) would not be expected to be tolerant to mdm100 peptides presented by H-$2K^b$ class I molecules, and it should be possible to isolate high avidity CTL. Thus, allo-restricted CTL were generated by stimulating naive BALB/c splenocytes with peptide-coated RMA-S (H-$2^b$) and T2-$K^b$ cells. Thirtythree CD8⁺ CTL clones were isolated which lysed RMA-S and T2-$K^b$ cells only when they were coated with mdm100 peptides, but not when they were coated with other H-$2^b$ class I binding peptides (FIGS. 3B and C). Syngeneic P815 cells (H-$2^d$) were unable to present the mdm100 peptide to these H-$2^d$-derived CTL clones. Peptide titration experiments revealed that 16 clones were of high "avidity" requiring $10^{-12}$ to $10^{-14}$ molar peptide concentration for half maximal target cell lysis (FIG. 3A). In contrast, 17 CTL clones were of low "avidity" requiring $10^{-8}$ to $10^{-9}$ molar peptide concentration (FIG. 3A).

Figure 3C:
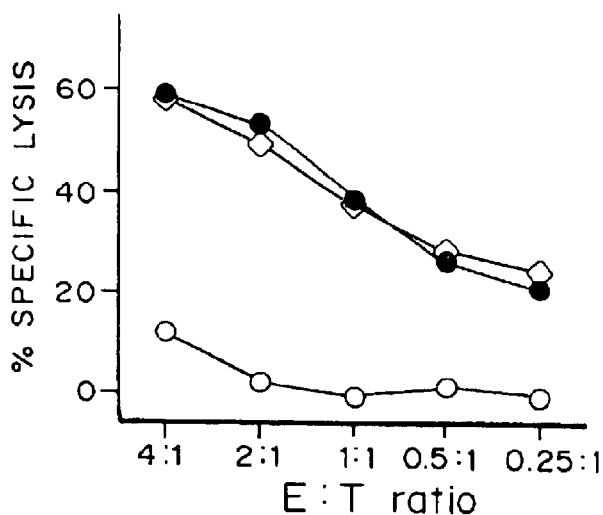
Figure 3D:
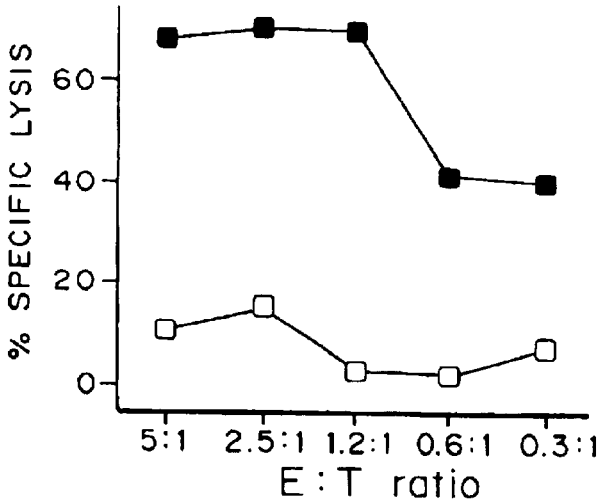

Allo-restricted CTL lyse tumor cells but not normal cells: The avidity of CTL clones was functionally important, since it determined the level of tumor cell lysis. All high avidity CTL clones efficiently killed RMA lymphoma cells (H-$2^b$), whilst lysis by all low avidity CTL clones was inefficient (FIGS. 3B and C). To determine whether high avidity CTL could discriminate between transformed and normal cells, we used dendritic cells (DC) as targets because they express high levels of MHC class I molecules as well as co-stimulatory molecules that are important for T cell activation (Steinman (1991) *Ann. Rev. Immunol.* 9, 271–296). The mdm-2 expression levels in DC have not yet been determined, but they might be similar to those found in tissues that consist primarily of non-proliferating cells. For example brain, heart and muscle contained considerable levels of mdm-2 RNA (Fakharzadeh et al (1991) *EMBO J.* 10, 1565–1569), although the levels were higher in tissues with a high proliferation index such as testis and thymus. FIG. 3D shows that the levels of mdm-2 expression in DC were insufficient to trigger lysis by high avidity CTL clones. Importantly, DC coated with the mdm100 peptide were efficiently lysed, indicating that these cells were not inherently resistant to CTL mediated killing (FIG. 3D). These in vitro experiments indicated that high avidity CTL could discriminate between transformed RMA tumor cells and normal dendritic cells. In vivo experiments also suggested that normal tissues were not attacked by high avidity CTL, since intravenous injection of $10^7$ CTL on three consecutive days was well tolerated by H-2$K^b$-positive C57BL/6 mice.

Figure 4B:
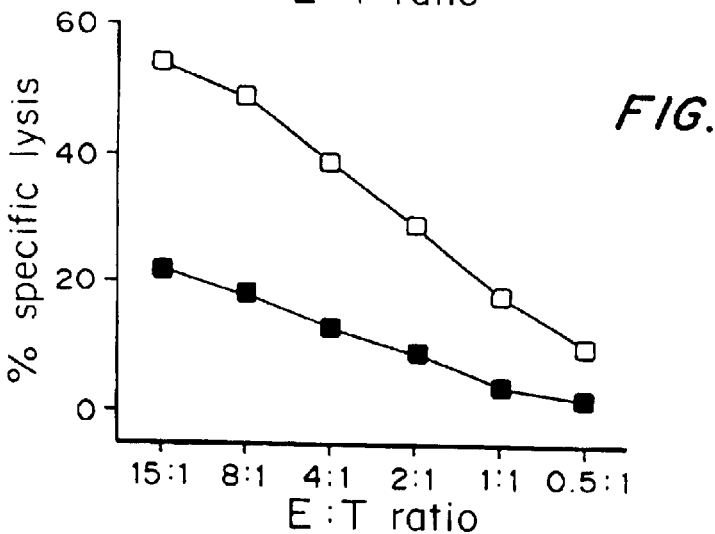

Tumor cell recognition by high avidity CTL was not limited to RMA lymphoma cells, but was also seen against B16 melanoma cells. However, melanoma recognition was dependent upon the levels of MHC class I expression. CTL killing was observed against the $K^b$-positive B16-F10 melanoma variant (FIG. 4B), whilst the $K^b$-negative B16-F1 variant was resistant to CTL lysis (FIG. 4A). The relative inefficient lysis of C16-F10 (FIG. 4B) compared to RMA (FIG. 3C) correlated with low and high levels of $K^b$ expression in these tumor cells. Increasing the density of $K^b$/peptide ligands by coating B16-F10 cells with mdm100 peptides resulted in enhanced CTL killing (FIG. 4B).

Evidence that the mdm100 peptide is naturally produced in tumor cells: The experiments described above have shown that CTL clones raised against the synthetic mdm100 peptide were able to recognise $K^b$-positive tumor cells. To address whether fortuitous cross-recognition of unrelated peptides accounted for CTL recognition of tumor cells, low molecular weight peptides were isolated from RMA cells and separated by reverse phase HPLC. Individual HPLC fractions were collected and used to coat T2-$K^b$ cells, which were then used as CTL targets. Only fraction 31 and 29 contained CTL recognised peptides (FIG. 5B). HPLC separation of synthetic mdm10 peptides revealed a major peptide peak in fraction 31 and minor peaks in fraction 29 (FIG. 5A). Mass-spectrometry revealed that fraction 31 contained the mdm100 peptide (YAMIYRNL; SEQ ID No 1) and fraction 29 contained the same peptide with an oxidised methionine at position 3. The co-elution of synthetic and naturally produced peptides strongly suggest that RMA tumor cells naturally produce the mdm100 peptide. The oxidised version of this peptide is probably not naturally produced, but might be the product of methionine oxidation during the TFA isolation procedure.

Allo-restricted CTL can delay tumor growth in H-$2^b$ mice: High avidity CTL were tested for their ability to control the growth of RMA lymphoma and B16-F10 melanoma tumors in vivo. C57BL/6 mice injected with RMA cells developed tumors at day 9 and died of large tumor burden within 14–15 days (FIGS. 6A and B). In contrast, tumor development was completely inhibited for 15–17 days in mice that were injected with RMA cells and CTL. The level of tumor protection was dose dependent and greater in mice injected with a large dose of CTL (FIG. 6A), compared to mice injected with a low dose of CTL (FIG. 6B). Similar results were obtained with the B16-F10 melanoma. Mice injected with B16-F10 cells only developed tumors after 8 days and died of tumor burden after 11–13 days, whilst mice injected with B16-F10 cells and CTL were tumor free until day 15 (FIG. 6C). Immune responses of recipient H-$2^b$ mice against the injected H-$2^d$-derived CTL clones is expected to limit their half life in vivo, and may explain why tumor protection was not complete. Further experiments will reveal to what extent immunosuppression of recipient mice can enhance tumor protection by transferred CTL clones. The experiments described here have established that allo-restricted CTL clones specific for peptides derived from the normal mdm-2 protein can control the growth of lymphoma and melanoma tumors in vivo.

This work demonstrates that it is possible to circumvent self tolerance by exploiting specificities present in the allo-restricted CTL repertoire. CTL clones specific for a peptide presented by non-self H-$2K^b$ class I molecules were obtained from the allo-restricted repertoire of BALB/c mice. Approximately 50% of the CTL clones were of high avidity and efficiently recognised mdm-2 expressing tumor cells, whilst low avidity CTL only recognised targets coated with synthetic peptides. The high avidity CTL clones displayed tumor-specificity and did not lyse dendritic cells or Con-A stimulated T cell blast in vitro. Intravenous injection of high avidity CTL clones was well tolerated by H-$2^b$ recipient mice.

It has been found that the repertoire of H-$2^b$ mice was deleted of high avidity CTL specific for the mdm100 peptide. This peptide stimulated only low avidity CTL that did not recognise mdm-2 expressing tumor cells. Therefore, the isolation of CTL capable of recognising tumor cells was constrained by tolerance to the mdm-2 protein. Similarly, targeting of tumors overexpressing normal p53 protein was also limited by CTL tolerance. In a series of experiments the CTL repertoire of HLA-A0201 transgenic mice was exploited to circumvent tolerance to human p53 (Theobald et al (1995) *Proc. Natl. Acad. Sci. USA* 92, 11993–11997). The CTL repertoire of these transgenic mice was tolerant only to murine p53 peptides. Two p53 peptides with sequence differences between man and mouse were found to stimulate high avidity CTL that recognised HLA-A0201 positive tumor cells but not dendritic cells. These studies showed that HLA transgenic mice can be exploited to generate murine CTL against human tumors overexpressing cellular proteins. This approach is dependent upon the availability of transgenic mice, and is limited to peptides with sequence differences between man and mouse. The advantage of the approach described herein is that CTL can be generated against any peptide expressed at elevated levels in tumors. Furthermore, the Theobald et al approach is dependent on differences between the human and mouse peptide; it uses mouse responder T cells to treat humans, and depends on there being proteins with differences between human and mouse as the targets.

Can allo-restricted CTL clones be exploited for adoptive tumor immunotherapy? Adoptive immunotherapy with these CTL clones is most likely to be effective in immunosuppressed cancer patients. For example, patients with chronic myeloid leukaemia (CML) are ideally suited for immunotherapy with allo-restricted CTL clones. CML patients frequently receive allogeneic bone marrow transplants, which requires immunosuppression in order to favour bone marrow engraftment. It has been known for some time that the prognosis of these patients is improved when donor derived T lymphocytes mount an immune response against patient's leukaemic cells (Goldman (1989) *Bone Marrow Transplant*

1, 133–134). However, this graft versus leukaemia reaction is often associated with detrimental graft versus host disease. The murine experiments described here indicate that it is possible to generate allo-restricted CTL clones that can specifically kill leukaemic cells. These results indicate that it should be possible to isolate human CTL clones specific for peptides presented at elevated levels in leukaemic cells. Such CTL clones can be used for adoptive immunotherapy of CML patients, and would mediate anti-leukaemia effects without causing graft versus host disease.

Thus, in this example we have investigated whether CTL can be raised against a ubiquitously expressed self protein, mdm-2, which is frequently overexpressed in tumors. The observation that T cell tolerance is self MHC-restricted was exploited to generate CTL specific for an mdm-2 derived peptide presented by non-self MHC class I molecules. Thus, the allo-restricted T cell repertoire of H-$2^d$ mice was used to isolate CTL specific for the mdm100 peptide presented by allogeneic H-$2K^b$ class I molecules. In vitro, these CTL discriminated between transformed and normal cells, killing specifically $K^b$-positive melanoma and lymphoma tumors but not $K^b$-expressing dendritic cells. In vivo, the CTL showed anti-tumor activity and delayed the growth of melanoma as well as lymphoma tumors in H-$2^b$ recipient mice. These experiments show that it is possible to circumvent T cell tolerance to ubiquitously expressed self antigens, and to target CTL responses against tumors expressing elevated levels of structurally unaltered proteins.

EXAMPLE 2

Identification of CTL Epitopes in HIV Proteins and in Tumour-Associated Proteins In order to serve as CTL targets peptides have to (i) be able to bind to HLA class I molecules; (ii) be able to stimulate CTL; (iii) be produced by natural antigen processing. These three requirements are tested experimentally.
(i) Identification of Peptides in HIV Proteins or in Tumour-associated Proteins which Bind to HLA Class I Molecules Peptide binding motifs have been identified for a large number of HLA class I molecules (11). These binding motifs are used to screen the sequences of HIV proteins or tumour-associated proteins. Motif-containing peptides are synthesised and the binding to the appropriated class I alleles is analysed. To analyse peptide binding, HLA class I molecules are expressed in the peptide loading mutant cell line T2 of human origin. T2 cells express naturally HLA-A0201 class I molecules. The expression of other HLA class I molecules (eg A1, B7 etc) is achieved by transfecting corresponding class I genes into T2 cells. Since T2 cells have a peptide loading defect, they express only low levels of peptide-containing class I molecules on their cell surface. However, if class I binding peptides are present in the culture medium, the levels of MHC class I expression are enhanced. The enhanced levels of class I expression is detected by staining T2 cells with HLA class I-specific antibodies, followed by analysis with a fluorescence activated cell sorter. Peptide-titration experiments reveal the efficiency of class I binding of individual peptides.

As an alternative to the described peptide-binding assay using intact T2 cells, binding assays are performed in cell lysates. Lysates of metabolically labelled T2 cells are incubated overnight at 4° C. in the presence of test peptides. Antibodies specific for conformationally correctly folded HLA class I molecules are used for immunoprecipitation. Only few conformationally folded class I molecules are detectable when T2 cell lysates are incubated in the absence of class I binding peptides. In contrast, if test peptides bind to class I molecules, this will stabilise their conformation. Consequently, increased levels of radiolabelled class I molecules are immunoprecipitated from T2 cell lysates incubated with class I binding peptides.

Radioactively labelled MHC class I molecules are not necessarily required to measure peptide binding. For example, known class I binding peptides can be labelled by iodination or by biotinylation and serve as indicator peptides in competition experiments. Thus, lysates from T2 cells containing HLA class I molecules are incubated with labelled indicator peptides together with varying concentrations of unlabelled test peptides. Test peptides which bind to HLA class I molecules successfully inhibit binding of indicator peptides. This results in a reduction of HLA class I molecules containing labelled indicator peptides. Thus, the amount of labelled indicator peptides detectable by immunoprecipitation with antibodies specific for conformationally correctly folded class I molecules is decreased.

T2 cells are not the only source of HLA class I molecules for binding assays. Drosophila cells represent an alternative source. Drosophila cells are transfected with human β2 microglobulin in conjunction with genes encoding various HLA class I alleles. Since Drosophila cells do not contain the TAP proteins required for peptide transport and MHC peptide loading, the transfected class I alleles are not naturally loaded via transporter, and so can be artificially loaded with peptides onto the surface. Thus, the conformation of class I molecules in lysates of transfected Drosophila cells is unstable in the absence of HLA binding peptides. Binding assays in lysates of Drosophila cells are performed under the same conditions as described for lysates prepared from T2 cells.
(ii) Stimulation of Peptide-Specific, Allo-restricted CTL Test peptides which bind efficiently to HLA class I molecules (see above) are used to stimulate CTL responses from healthy, HLA unrelated individuals. Allo-reactive CTL responses against peptides other than the test peptides are avoided. The probability of stimulating CTL against test peptides is increased if the majority of HLA molecules expressed by the stimulator cells have test peptides in their binding groove. Thus, the approach is to express by transfection the same HLA class I molecules in various human and non-human cells, and to load them with class I binding test peptides. These peptide loaded cells are then used to stimulate CTL from PBMC of HLA unrelated healthy individuals. The PBMC are stimulated every 1–2 weeks with different human and non-human cell types expressing the same HLA molecule. This decreases the probability of stimulating CTL against irrelevant peptides because the different human and non-human cell types most likely present different sets of these irrelevant peptides.

The following cell types are suitable for expression of HLA class I molecules and for CTL stimulation: the human cell lines T2 and C1R, the mouse cell lines RMA, RMA-S and P1HTR, and Drosophila cells that were transfected to express not only HLA class I molecules but also molecules that are important for T cell costimulation such as B7.1, B7.2, ICAM1 and LFA3.

To achieve high levels of MHC occupancy with test peptides the HLA transfected T2, RMA-S and Drosophila cells are particularly suitable. These cell types do not express functional TAP peptide transporter molecules and consequently express a large proportion of peptide deficient MHC molecules which can be loaded with exogenously added peptides. Thus, these cells are incubated overnight with 100 μM of test peptides and then used to stimulate CTL using PBMC of healthy donors. To achieve high levels of MHC occupancy with test peptides in the normal cell lines C1R, RMA and P1HTR, these cells are treated with a buffer containing 0.2 M acetic acid and 0.2 M sodium chloride at pH 3–4 for approximately 1 minute to denature the peptide containing MHC class I molecules on the surface of these cells. The cells are then incubated at neutral pH in medium containing human β2-microglobulin and 100–200 μM of test peptides. During this incubation, a large proportion of HLA class I molecules refold and contain the test peptide in their binding groove.

CTL cultures are initiated in 24 well plates using $5 \times 10^6$ responder PBMC obtained from buffy coat blood packs and $10^6$ irradiated, peptide-loaded stimulator cells per well. The culture medium consists of RPMI, 10% FCS, 10% culture supernatant of anti-CD4 monoclonal antibodies and 10 U/ml recombinant IL-2. After one week the responding CTL are restimulated in micro-cultures in 96 well plates. Each well contains $2 \times 10^5$ irradiated autologous PBMC feeder cells and $10^5$ irradiated peptide-loaded stimulator cells. Varying numbers of responder CTL starting from approximately $5 \times 10^4$ to $5 \times 10^2$ are seeded per micro-culture. Replica cultures of 24 wells are set up for each responder cell number. The micro-cultures are restimulated with fresh irradiated PBMC and peptide-loaded stimulator cells after 10–14 days. 7 days after the last stimulation, the CTL from individual micro-cultures are analysed in a $^{51}$Cr release assay against T2 cells expressing the appropriate HLA-class I molecules presenting the test peptides that are used to generate the CTL or presenting irrelevant control peptides. Micro-cultures that show preferential killing of T2 cells coated with test peptides over T2 cells coated with irrelevant peptides are expanded to confirm the CTL specificity. At the same time, some of these CTL are used for limiting dilution cloning on 96 well plates using the same numbers of feeder cells and stimulator cells as for the micro-cultures described above. 1 to 0.5 CTL are seeded per well. The specificity of CTL clones is confirmed using T2 target cells coated with relevant and irrelevant peptides.

(iii) Identification of Peptides Produced by Natural Antigen Processing

Whether test peptides that bind well to HLA class I molecules ((i) above) and that stimulate CTL responses ((ii) above) are produced by natural antigen processing is determined. Initially, peptides are selected by screening the sequences of HIV proteins and of tumour-associated proteins for the presence of MHC class I binding motifs. The work described in sections (i)–(ii) above shows that selected test peptides can bind to class I molecules and can stimulate peptide-specific CTL. Whether natural antigen processing leads to the MHC class I presentation of these peptides is determined. Peptide-specific CTL lines and clones are tested against target cells expressing relevant HIV proteins or tumour-associated proteins endogenously. Thus, human C1R cells are doubly transfected with the relevant HLA class I genes and the genes encoding HIV proteins or tumour-associated protein. CTL lysis of doubly transfected C1R target cells in the absence of lysis of singly transfected cells shows that natural processing of endogenously expressed proteins produces the peptides recognised by these CTL clones.

EXAMPLE 3

Adoptive Immunotherapy Using CTL in Humans

Similar in vitro stimulation conditions to those described in Example 2 for the mouse produce human allo-restricted CTL. Allo-restricted CTL recognising peptides derived from HIV proteins or from tumour-associated proteins presented by the HLA-A0201 class I molecule are generated. (Allo-restricted CTL recognising peptides presented by HLA-A1 and HLA-B7 will be isolated may also be used.) These three HLA alleles are among the most frequent in Caucasian populations and there is a high probability that any one individual will express at least one of the three alleles. This means, that CTL clones restricted by these three HLA alleles is useful for adoptive immunotherapy of the majority of individuals of a Caucasian population. The CTL clones are used as an adjuvant to chemotherapy in treating the cancer.

For adoptive immunotherapy of HIV infected individuals, peptides derived from HIV encoded proteins are exploited. Virus load is suppressed following administration of the CTL.

FIG. 7(A) shows the lysis of a CTL clone specific for a HLA-A0201-binding cyclin D1 peptide (101–110). The CTL clone was obtained from HLA-A2 negative PBMC.

FIG. 7(B) shows the lysis of a CTL clone specific for a HLA-A0201-binding cyclin D1 peptide (228–234). The CTL clone was obtained from HLA-A2 negative PBMC.

The experiments with the cyclin D1-derived peptides show that it is possible to generate peptide-specific CTL from healthy donors by stimulation of PBMC with MHC-mismatched antigen presenting cells. These CTL are specific for cyclin D1 peptides presented by HLA-A0201 class I molecules which are expressed by the antigen presenting cells used for CTL stimulation but not by cells of the CTL donor. Thus, it is clearly possible to isolate peptide-specific, allo-restricted CTL from normal individuals. If the selected peptides are produced in the tumour cells, the peptide-specific, allo-restricted CTL displays tumour cell killing.

References

1. Kast, W. M., R. Offringa, P. J. Peters, A. C. Voordouw, R. H. Meloen, A. J. van der Eb, and C. J. Melief (1989) "Eradication of adenovirus E1-induced tumors by E1A-specific cytotoxic T lymphocytes" Cell 59, No. 4, 603–14.
2. Kawakami, Y., S. Eliyahu, C. H. Delgado, P. F. Robbins, K. Sakaguchi, E. Appella, J. R. Yannelli, G. J. Adema, T. Miki, and S. A. Rosenberg (1994) "Identification of a human melanoma antigen recognized by tumor-infiltrating lymphocytes associated with in vivo tumor rejection" Proc Natl Acad Sci USA 91, No. 14, 6458–62.
3. Nowak, M. A., R. M. May, R. E. Phillips, S. Rowland Jones, D. G. Lalloo, S. McAdam, P. Klenerman, B. Koppe, K. Sigmund, C. R. Bangham et al (1995) "Antigenic oscillations and shifting immunodominance in HIV-1 infections [see comments]" Nature 375, No. 6532, 606–11.
4. Riddell, S. R., K. S. Watanabe, J. M. Goodrich, C. R. Li, M. E. Agha, and P. D. Greenberg (1992) "Restoration of viral immunity in immunodeficient humans by the adoptive transfer of T cell clones [see commnents]" Science 257, No. 5067, 238–41.
5. van Lochem, E., B. de Gast, and E. Goulmy (1992) "In vitro separation of host specific graft-versus-host and graft-versus-leukemia cytotoxic T cell activities" Bone-Marrow-Transplant 10, No. 2, 181–3.
6. Faber, L. M., S. A. van Luxemburg Heijs, R. Willemze, and J. H. Falkenburg (1992) "Generation of leukemia-reactive cytotoxic T lymphocyte clones from the HLA-identical bone marrow donor of a patient with leukemia" J-Exp-Med 176, No. 5, 1283–9.
7. Falkenburg, J. H., L. M. Faber, M. van den Elshout, S. A. van Luxemburg Heijs, A. Hooftman den Otter, W. M.

Smit, P. J. Voogt, and R. Willemze (1993) "Generation of donor-derived antileukemic cytotoxic T-lymphocyte responses for treatment of relapsed leukemia after allogeneic HLA-identical bone marrow transplantation" *J-Immunother* 14, No. 4, 305–9 issn. 1053–8550.

8. Heath, W. R., M. E. Hurd, F. R. Carbone, and L. A. Sherman (1989) "Peptide-dependent recognition of H-2Kb by alloreactive cytotoxic T lymphocytes" *Nature* 341, No. 6244, 749–52.

9. Rojo, S., and J. A. Lopez de Castro (1991) "Peptide-mediated allorecognition of HLA-B27 by cytotoxic T lymphocytes" *Int J Cancer Suppl* 6, 10–3.

10. von Boehmer, H. (1992) "Thymic selection: a matter of life and death" *Immunol-Today* 13, No. 11, 454–8.

11. Rammensee, H. G., T. Friede, and S. Stevanoviic (1995) "MHC ligands and peptide motifs: first listing" *Immunogenetics* 41, No. 4, 178–228.

12. Walker, B. D., and F. Plata (1990) "Cytotoxic T lymphocytes against HIV" *AIDS* 4, No. 3, 177–84.

13. Nixon, D. F., and A. J. McMichael (1991) "Cytotoxic T-cell recognition of HIV proteins and peptides [editorial]" *AIDS* 5, No. 9, 1049–59.

14. Bakker, A. B. H., M. W. J. Schreurs, A. J. de Boer, Y. Kawakami, S. A. Rosenberg, G. J. Adema, and C. G. Figdor (1994) "Melanocyte lineage-specific antigen gp100 is recognized by melanoma-derived tumor-infiltrating lymphocytes" *J Exp Med* 179, 1005–1009.

15. Boel, P., C. Wildmann, M. L. Sensi, R. Brasseur, J. C. Renauld, P. Coulie, T. Boon, and P. van der Bruggen (1995) "BAGE: a new gene encoding an antigen recognized on human melanomas by cytolytic T lymphocytes" *Immunity* 2, No. 2, 167–75 issn. 1074–7613.

16. Cox, A. L., J. Skipper, Y. Chen, R. A. Henderson, T. L. Darrow, J. Shabanowitz, V. H. Engelhard, D. F. Hunt, and C. L. Slingluff Jr (1994) "Identification of a peptide recognised by five melanoma-specific human cytotoxic T cell lines" *Science* 264, 716–719.

17. Kawakami, Y., S. Eliyahu, C. H. Delgado, P. F. Robbins, L. Rivoltini, S. L. Topalian, T. Miki, and S. A. Rosenberg (1994) "Cloning of the gene coding for a shared human-melanoma antigen recognized by autologous T-cells infiltrating into tumor" *Proc Natl Acad Sci USA* 91, No. 9, 3515–3519.

18. Kawakami, Y., S. Eliyahu, K. Sakaguhi, P. F. Robbins, L. Rivoltini, J. R. Yannelli, E. Appella, and S. A. Rosenberg (1994) "Identification of the immunodominant peptides of the MART-1 human melanoma antigen recognized by the majority of HLA-A2-restricted tumor infiltrating lymphocytes" *J Exp Med* 180, 347–352.

19. Traversari, C., P. van der Bruggen, I. F. Luescher, C. Lurquin, P. Chomez, A. Van Pel, E. de Plaen, A. Amar-Costesec, and T. Boon (1992) "A nonapeptide encoded by human gene MAGE-1 is recognized on HLA-A1 by cytolytic T lymphocytes directed against tumor antigen MZ2-E" *J. Exp. Med.* 176, 1453–1457.

20. van der Bruggen, P., C. Traversari, P. Chomez, C. Lurquin, E. de Plaen, B. van den Eynde, A. Knuth, and T. Boon (1991) "A gene encoding an antigen recognized by cytolytic T lymphocytes on a human melanoma" *Science* 254, 1643–1647.

21. Wolfel, T., A. Van Pel, V. Brichard, J. Schneider, B. Seliger, K. Meyer zum Buischenfelde, and T. Boon (1994) "Two tyrosinase nonapeptides recognized on HLA-A2 melanomas by autologous cytolytic T lymphocytes" *Eur J Immunol* 24, 759–764.

What is claimed is:

1. A method of killing cells in a patient, the method comprising, administering to the patient a therapeutically effective amount of cytotoxic T lymphocytes (CTL), wherein the CTLs have a different HLA class I complex (or equivalent) than the cells to be killed, and the CTLs specifically recognize a peptide portion of an antigen on the cells to be killed when the peptide is presented by the HLA class I complex (or equivalent) on the surface of cells to be killed, wherein the HLA class I complex (or equivalent) type presenting the peptide in the cells to be killed is not present in the CTLS to be administered to the patient, and the antigen is present at an abnormally elevated amount in the patient, and the CTLs kill the presenting cells.

2. A method according to claim 1 wherein the CTL are a clonal population of CTL.

3. A method according to claim 1 wherein the CTL are substantially free of other cell types.

4. A method according to claim 1 wherein the antigen is present at an abnormally elevated amount in the cells to be killed compared to other cells.

5. A method according to claim 1 wherein the cells to be killed are cancer cells.

6. A method according to claim 5 wherein the cancer is selected from the group consisting of breast cancer; bladder cancer; lung cancer; prostate cancer; thyroid cancer; leukemias; lymphomas; colon cancer; glioma; seminoma; liver cancer; pancreatic cancer; renal cancer; cervical cancer; testicular cancer; head and neck cancer; ovarian cancer; neuroblastoma and melanoma.

7. A method according to claim 1 further comprising the step of determining the HLA class I (or equivalent) molecule type of the patient prior to administration of the CTL.

8. A method according to claim 7 wherein the type is determined using DNA typing.

9. A method according to claim 1 wherein the patient is human.

10. A method according to claim 7 wherein the cytotoxic T lymphocyte is selected from a library of CTL clones, the library comprising a plurality of CTL clones derived from individuals with differing HLA class I (or equivalent) molecule type and each CTL clone recognises the cells to be killed.

11. A method according to claim 10 wherein each CTL clone recognises at least part of the pentide portion of the antigen on the cells to be killed.

12. The method of claim 6, wherein the leukemia is selected from the group consisting of chronic myeloid leukemia (CML), acute lymphocytic leukemia (ALL), acute myeloid leukemia (AML), and promyeloid leukemia (PML).

* * * * *